(12) United States Patent
Cerda et al.

(10) Patent No.: US 9,410,926 B2
(45) Date of Patent: Aug. 9, 2016

(54) METHODS AND APPARATUS FOR IDENTIFICATION OF POLYMERIC SPECIES FROM MASS SPECTROMETRY OUTPUT

(71) Applicant: PerkinElmer Health Sciences, Inc., Waltham, MA (US)

(72) Inventors: Blas Cerda, Milford, MA (US); Vsevolod Sergey Rakov, New Haven, CT (US); Hayley E. Crowe, West Haven, CT (US)

(73) Assignee: PERKINELMER HEALTH SCIENCES, INC., Waltham, MA (US)

( * ) Notice: Subject to any disclaimer, the term of this patent is extended or adjusted under 35 U.S.C. 154(b) by 602 days.

(21) Appl. No.: 13/751,871

(22) Filed: Jan. 28, 2013

(65) Prior Publication Data
US 2014/0045273 A1    Feb. 13, 2014

Related U.S. Application Data

(60) Provisional application No. 61/681,575, filed on Aug. 9, 2012, provisional application No. 61/696,071, filed on Aug. 31, 2012.

(51) Int. Cl.
*G01N 27/62* (2006.01)
*G06F 19/00* (2011.01)

(52) U.S. Cl.
CPC .............. *G01N 27/62* (2013.01); *G06F 19/703* (2013.01); *G06F 19/705* (2013.01); *Y10T 436/24* (2015.01)

(58) Field of Classification Search
CPC ............ G01N 30/88; G01N 2030/885; G01N 2030/8831; G01N 27/62; Y10T 436/24; G06F 19/703; G06F 19/705
See application file for complete search history.

(56) References Cited

U.S. PATENT DOCUMENTS

| | | |
|---|---|---|
| 2005/0164324 A1 | 7/2005 | Gygi |
| 2011/0143951 A1 | 6/2011 | Thompson |
| 2012/0197535 A1 | 8/2012 | Goodlett et al. |

OTHER PUBLICATIONS

Kind, Tobias et al. "Advances in structure elucidation of small molecules using mass spectrometry." Bioanal Rev (2010) 2 23-60.*
Marcotte, Edward M. et al. "A census of protein repeats." JMB (1998) 293 151-160.*
AccuTOF product document. 2003.*
AxION 2 TOF MS User's Guide, PerkinElmer, 2012, 136 pages.
Domon et al., Mass Spectrometry and Protein Analysis, Science, vol. 312, No. 5771, Apr. 14, 2006, pp. 212-217.
International Search Report, PCT/US13/023442, Nov. 22, 2013, 4 pages.

(Continued)

*Primary Examiner* — Christopher A Hixson
(74) *Attorney, Agent, or Firm* — Choate, Hall & Stewart-LLP; William R. Haulbrook

(57) ABSTRACT

Methods and apparatus are provided for the identification of one or more candidate chemical formulas from mass spectrometry data corresponding to an unidentified chemical compound. By restricting the generation of candidate formulas to those having repeating units and/or end units with specified limitations, the methods and apparatus may more efficiently iteratively search for a chemical formula having matching mass spectrometry output within a threshold tolerance. In another aspect, methods and apparatus are provided for the identification of one or more candidate chemical formulas from mass spectrometry data based at least in part upon neutral loss.

25 Claims, 20 Drawing Sheets

(56) References Cited

OTHER PUBLICATIONS

Schroeder et al., A Neutral Loss Activation Method for Improved Phosphopeptide Sequence Analysis by Quadrupole Ion Trap Mass Spectrometry, Analystical Chemistry, vol. 76, No. 13, Jul. 1, 2004, pp. 3590-3598.

Written Opinion, PCT/US2013/023442, Nov. 22, 2013, 7 pages.

* cited by examiner

FIG. 3C

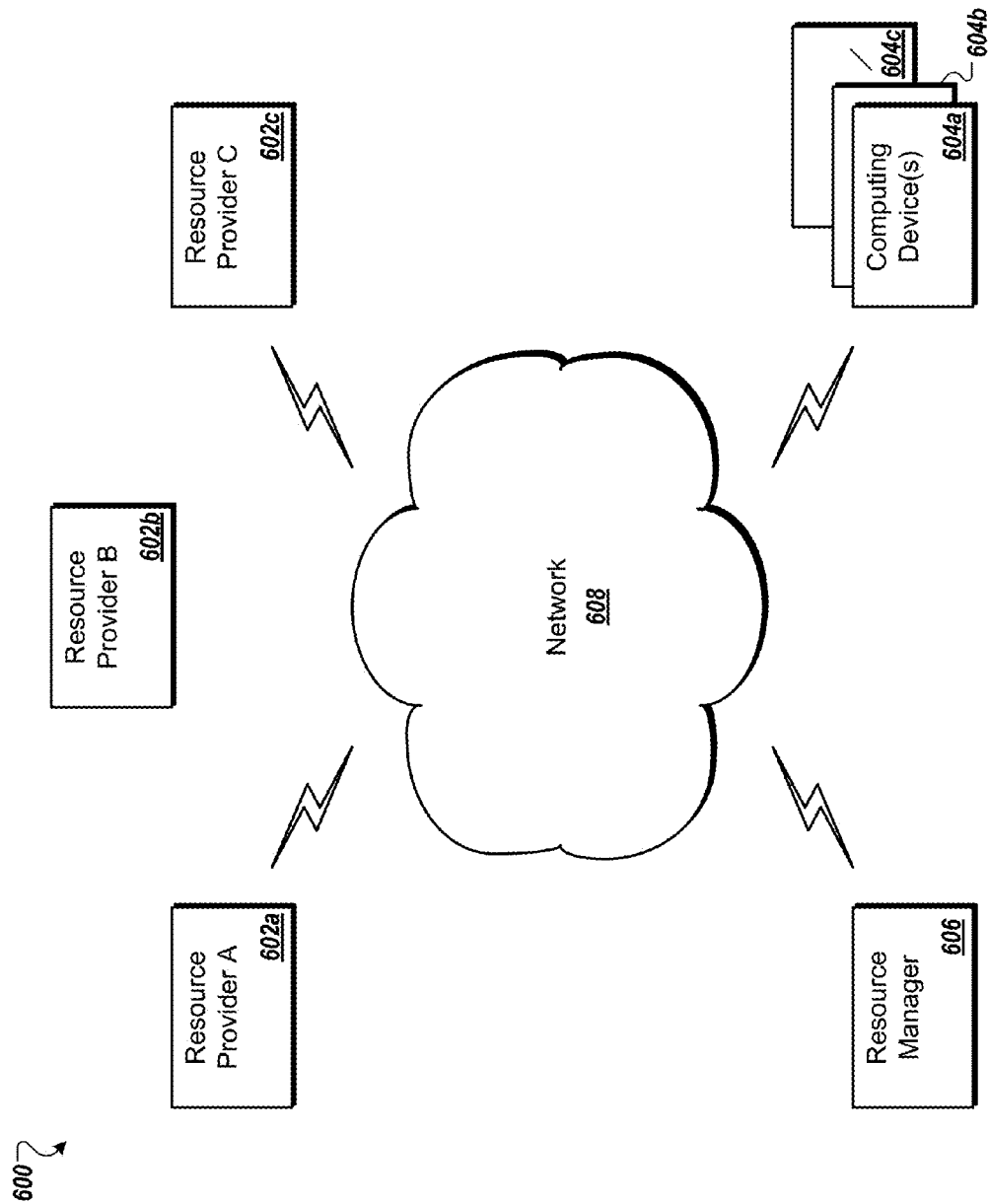

METHODS AND APPARATUS FOR IDENTIFICATION OF POLYMERIC SPECIES FROM MASS SPECTROMETRY OUTPUT

RELATED APPLICATIONS

The present application claims priority to and the benefit of U.S. Provisional Patent Application No. 61/681,575 entitled "Methods and Apparatus for Identification of Polymeric Species from Mass Spectrometry Output" and filed Aug. 9, 2012, and U.S. Provisional Patent Application No. 61/696,071 entitled "Methods and Apparatus for Identification of Polymeric Species from Mass Spectrometry Output" and filed Aug. 31, 2012, the contents of each of which is hereby incorporated by reference in its entirety.

BACKGROUND

Mass Spectrometry (MS) is an analytical tool that measures the mass-to-charge ratio of charged particles, and is widely used for the qualitative and quantitative analysis of chemical compounds including compound identification, as well of interrogation of compound's structure, selective reactivity, stability, etc. Commercially available modern mass spectrometers not only employ different methods of separation of ions, but also vary in evaporation/ionization techniques, as well as detection schemes. This results in an ever-broadening range of scientific applications based on or related to mass spectrometric measurements.

The first generation of commercial mass spectrometers for analytical chemistry used an electron impact ionization technique, which, in its optimal mode of 70 eV electron energy, routinely overexcited analyte molecules, resulting in a rapid gas phase unimolecular decomposition of significant portion of parent ions. This produced a characteristic analyte "signature" spectrum—a mixture of peaks of parent ion and its fragments. These spectra were quickly recorded and organized into the so-called MS-libraries, used even today as an identification tool for mass spectrometry. However, electron impact, a gas-phase ionization technique, relies on up-front evaporation of a sample, easily realized only for volatile low-to-medium mass range analyte molecules. For analytes above 300 Da not only evaporation is problematic, but also electron-impact induced fragmentation becomes too complex.

Discovery of modern "soft" ionization techniques which produce "cold" analyte molecular ions, starting with chemical ionization, solved the problem of post-ionization dissociation and complexity of the immediate spectra, but added to the ambiguity of the parent ion identity assignment. Without the background dissociation, the "signature" feature of an analyte molecular ion was gone. But the only real advance of chemical ionization was to eliminate the post-ionization dissociation. Since it was the first of the soft techniques, scientists had roughly a decade to find ways to re-introduce dissociation into the mass spectrometry—hoping to regain the "signature" feature as a tool to solve the problem of analyte identification. It came in the form of commercially-developed tandem mass spectrometers: devices in which creation of the analyte molecular ion is separated (in space or time) from the event of its fragmentation.

Chemical (charge transfer) ionization saw about a decade of its renaissance between 1975 and 1985, before the advantages of new ionization techniques opened up a new era in analytical mass spectrometry. Fast atom bombardment (FAB), electrospray ionization (ESI) and matrix assisted laser desorption ionization (MALDI) have coupled two principal steps involved in mass spectrometry analysis: evaporation and ionization, thus allowing for mass-spectral analysis of large molecules. It took the scientific community about a decade to catch up with the technology, culminating in the current explosion of mass spectrometry-based applications in analytical synthetic chemistry, pharmacology, ecology, biology, food science, etc.

Regardless of a compound's physical or chemical properties that are of ultimate scientific interest, the first goal of mass spectrometry is to establish the compound's identity. At the most basic level of identification, the molecular formula (elemental composition) of the ion needs to be determined Higher order information (molecular structure, conformation, stability, etc.) can be revealed through gas-phase chemistry in multi-stage mass spectrometry experiments, and/or in combination with "orthogonal" techniques, such as chromatography, electrophoresis, ion mobility, spectroscopy, etc. For relatively small molecules, knowledge of exact mass and relative abundance of isotopes may be sufficient to reveal molecular formula information, even in the absence of the background fragmentation. In any case, potential candidate molecular formulas need to be either referenced from previously established lists (databases) or generated by nested loop summations, realizing possible combinations of number of atoms of different types (carbon, oxygen, hydrogen, etc.) in attempt to match experimentally observed masses with required precision. Historically, the latter approach of generating formulas as atomic combinations was the only available approach. While the former approach of the so-called "known unknown" target analysis has gained popularity as databases of known compounds are publicly available and continue to grow, even today in special applications such as large polymer synthesis, information offered by public databases may not be sufficient to provide identification base for researcher's needs. In such cases, a mass spectrometry specialist still needs to revisit the old formula generation approach in an attempt to assign molecular formulas to experimentally observed mass spectrometric peaks. Unfortunately, current formula generator algorithms are based on nested loops and are inherently susceptible to exponential dependence of computational cost on (a) the number of atoms types assumed to be comprising the potential formula, and (b) of the mass of the target ion.

Algorithmic improvements to the molecular formula generation models remain very relevant even today, as a potential way to improve the first step of mass spectrometric investigations: identification of the atomic composition of ionic species.

SUMMARY

A software tool is provided for the identification of one or more candidate chemical formulas from mass spectrometry data corresponding to an unidentified chemical compound. By restricting the generation of candidate formulas to those having repeating units and/or end units with specified limitations, the software tool may more efficiently iteratively search for a chemical formula having matching mass spectrometry output within a threshold tolerance. In another aspect, a software tool is provided for the identification of one or more candidate chemical formulas from mass spectrometry data based at least in part upon neutral loss.

To aid in the speed and accuracy of identification of an unknown polymeric chemical compound from mass spectrometry data, where the unknown compound includes a repeating unit and one or more end units, a software tool for chemical formula identification is provided which identifies one or more candidate structures given the mass spectrometry data and additional data including: (i) identification of one or more candidate repeating units; (ii) identification of a set of chemical elements in the one or more end units; and/or (iii) identification of a maximum number of chemical elements in the one or more end units (e.g., maximum of each chemical element or maximum total chemical elements). In some implementations, the software tool provides a graphical user interface for performing the above identification. In some implementations, the software tool is used to identify an unknown polymeric species having a repeating unit that repeats at least three times. By restricting the generation of candidate formulas to those having repeating units and/or end units with specified limitations, the software tool may more efficiently iteratively search for a chemical formula including the repeating units plus end unit structures matching the mass spectrometry output within a threshold tolerance.

In some implementations, the software tool accepts both a repeating unit structure (or its exact mass) and a limitation upon the structure or composition of one or both end unit(s). For example, a user may limit the number of elements composing one or both end unit(s) to a maximum number of elements (e.g., 10). In another example, a user may limit the type of elements (e.g., the element species) to a particular set.

In another implementation, a software tool for chemical formula identification is provided for the identification of a chemical formula from mass spectrometry data based at least in part upon neutral loss, a mass difference between two mass spectral peaks due to processing such as front-end chemistry or gas-phase fragmentation which results in a loss of molecular formula. This software tool may increase accuracy or narrow a pool of potential candidates of chemical formulas in relation to the following examples: collision-induced disassociation in capillary-skimmer region of a TOF mass spectrometer; metabolites in bulk; front-end chemical reactions (e.g., reactions in a sample prior to mass spectrometry); and polymer identity in relation to exact mass of the repeating unit. In some implementations, the software tool provides a graphical user interface for performing the above identification.

In another implementation, a software tool for chemical formula identification is provided for the identification of a polymeric compound from mass spectrometry data by restricting the generation of candidate formulas to those having repeating units and/or end units with specified limitations and by identifying and using a measure of neutral loss to narrow a pool of potential candidates of chemical formulas.

In one aspect, the invention is directed to a method for identifying a species of an unidentified chemical compound including two or more repeating structural units, the method including accessing at least a portion of mass spectrometry data, where the portion of mass spectrometry data relates to a sample including the unidentified chemical compound, where the unidentified chemical compound includes (a) the two or more repeating structural units, and (b) at least one end unit. The method may include determining at least one of (a) a chemical formula of the repeating structural unit, and (b) an estimated weight of the two or more repeating structural units, and identifying, by a processor of a computing device, one or more candidate chemical formulas for the unidentified chemical compound based at least in part upon the mass spectrometry data, and based further in part on at least one of (a) the chemical formula of the repeating structural unit, and (b) the estimated weight.

In certain embodiments, each repeating structural unit of the two or more repeating structural units has a same chemical formula, and the at least one end unit has a chemical formula different than the chemical formula of the two or more repeating structural units.

In certain embodiments, the method includes determining a set of candidate chemical elements, where the chemical formula of any end unit of the at least one end unit consists of one or more elements of the set of candidate chemical elements. The method may include determining a maximum number of each chemical element of the set of candidate chemical elements, where the chemical formula of any end unit of the at least one end unit consists of no more than the maximum number of each chemical element of the set of candidate chemical elements. Identifying the one or more candidate chemical formulas for the unidentified chemical compound may include identifying the one or more candidate chemical formulas for unidentified chemical compound based further in part upon the set of candidate chemical elements.

In certain embodiments, the method includes identifying, from the portion of the mass spectrometry data, an estimated weight of the unidentified chemical compound, where identifying the one or more candidate chemical formulas for the unidentified chemical compound includes identifying the one or more candidate chemical formulas for the unidentified chemical compound based further in part upon the estimated weight of the unidentified chemical compound. Identifying the one or more candidate chemical formulas for the unidentified chemical compound may include iteratively adding combinations of possible element types to identify a number of potential element combinations for the one or more end units, where a calculated weight of each potential element combination of the number of potential element combinations, when summed with the estimated weight of the two or more repeating units, is within a threshold weight of the estimated weight of the unidentified chemical compound. The method may further include calculating the estimated weight of the two or more repeating units. Calculating the estimated weight may include calculating a weight of a first candidate chemical formula of the one or more candidate chemical formulas, and multiplying the weight of the first candidate chemical formula by a maximum potential number of repetitions.

In certain embodiments, the method includes, after identifying the one or more candidate chemical formulas for the unidentified chemical compound, for each candidate chemical formula of the one or more candidate chemical formulas: obtaining mass spectrometry data for the respective candidate chemical formula; and comparing theoretical spectral data of the mass spectrometry data for the respective candidate chemical formula to experimental spectral data of the portion of mass spectrometry data. The method may further include, based in part on at least one respective result of comparing the theoretical spectral data of the mass spectrometry data of each candidate chemical formula of the one or more candidate chemical formulas to the theoretical spectral data of the portion of mass spectrometry data, ranking the one or more candidate chemical formulas. The method may further include, for at least one candidate chemical formula of the one or more candidate chemical formulas, based in part upon a respective result of comparing the theoretical spectral data of the mass spectrometry data of the at least one candidate chemical formula to the experimental spectral data of the portion of mass spectrometry data, discarding a first candidate chemical formula of the at least one candidate chemical formula.

In certain embodiments, the method further includes presenting the one or more candidate chemical formulas to a user within a graphical user interface.

In one aspect, the invention is directed to a system including a processor; and a memory storing instructions thereon, where the instructions when executed cause the processor to access at least a portion of mass spectrometry data, where the portion of mass spectrometry data relates to a sample including an unidentified chemical compound, where the unidentified chemical compound includes (a) the two or more repeating structural units, and (b) at least one end unit. The instructions may cause the processor to determine at least one of (a) a chemical formula of the repeating structural unit, and (b) an estimated weight of the two or more repeating structural units. The instructions may cause the processor to identify one or more candidate chemical formulas for the unidentified chemical compound based at least in part upon the mass spectrometry data, and based further in part on at least one of (a) the chemical formula of the repeating structural unit, and (b) the estimated weight.

In certain embodiments, each repeating structural unit of the two or more repeating structural units has a same chemical formula, and the at least one end unit has a chemical formula different than the chemical formula of the two or more repeating structural units.

In certain embodiments, the instructions further cause the processor to determine a first candidate chemical formula of the one or more candidate chemical formulas is a neutral loss match to the unidentified chemical compound, the determining of the neutral loss match including accessing spectral data for the first candidate chemical formula, and, for each of a number of spectral peaks of the spectral data: calculating a respective mass difference between a theoretical mass of the first candidate chemical formula and a respective experimental mass corresponding to the spectral peak, and comparing the respective mass difference with a mass of each of one or more corresponding neutral molecular compositions to identify one or more candidate neutral molecular compositions corresponding to the spectral peak. The spectral data may include a collision-induced dissociation (CID) mass spectrum. Identifying at least the first candidate chemical formula may include identifying a second candidate chemical formula, the instructions further causing the processor to: determine the second candidate chemical formula is a neutral loss match to the unidentified chemical compound; and rank the first candidate chemical formula and the second candidate chemical formula as matches to the unknown chemical compound based in part upon similarity in neutral loss match. Identifying the one or more candidate neutral molecular compositions may include identifying that each candidate neutral molecular composition of the one or more candidate neutral molecular compositions includes a respective mass within range of a mass measurement accuracy of the respective experimental mass of the spectral peak.

In certain embodiments, determining the first candidate chemical formula is a neutral loss match to the unidentified chemical compound may include identifying that a stoichiometry of the first candidate chemical formula allows for at least a first candidate neutral molecular composition of the one or more candidate neutral molecular compositions. Identifying that a stoichiometry of the first candidate formula allows for the first candidate neutral molecular composition may include determining, for the first candidate neutral molecular composition, a number of atoms of each type in the first candidate chemical formula is greater than a number of atoms of each corresponding type in the candidate neutral loss composition.

In one aspect, the invention is directed to a non-transitory computer readable medium having instructions stored thereon that, when executed by a processor, cause the processor to perform operations including accessing at least a portion of mass spectrometry data, where the portion of mass spectrometry data relates to a sample including an unidentified chemical compound, where the unidentified chemical compound includes (a) the two or more repeating structural units, and (b) at least one end unit. The instructions may cause the processor to determine at least one of (a) a chemical formula of the repeating structural unit, and (b) an estimated weight of the two or more repeating structural units. The instructions may cause the processor to identify one or more candidate chemical formulas for the unidentified chemical compound based at least in part upon the mass spectrometry data, and based further in part on at least one of (a) the one or more candidate chemical formulas, and (b) the estimated weight.

In one aspect, the invention is directed to a method for identifying a species of an unidentified chemical compound, the method including accessing, by a processor of a computing device, mass spectrometry data for a sample including the unidentified chemical compound, identifying, by the processor, at least a first candidate chemical formula for the unidentified chemical compound based at least in part on the mass spectrometry data, accessing, by the processor, spectral data for the first candidate chemical formula; and determining, by the processor, the first candidate chemical formula is a neutral loss match to the unidentified chemical compound. The determining of the neutral loss match may include, for each of a number of spectral peaks of the spectral data: calculating a respective mass difference between a theoretical mass of the first candidate chemical formula and a respective experimental mass corresponding to the spectral peak, and comparing the respective mass difference with a mass of each of one or more corresponding neutral molecular compositions to identify one or more candidate neutral molecular compositions corresponding to the spectral peak.

In certain embodiments, the spectral data includes a collision-induced dissociation (CID) mass spectrum. Identifying at least the first candidate chemical formula may include identifying a second candidate chemical formula. The method may further include determining, by the processor, the second candidate chemical formula is a neutral loss match to the unidentified chemical compound; and ranking, by the processor, the first candidate chemical formula and the second candidate chemical formula as matches to the unknown chemical compound based in part upon similarity in neutral loss match.

In certain embodiments, identifying the one or more candidate neutral molecular compositions includes identifying that each candidate neutral molecular composition of the one or more candidate neutral molecular compositions includes a respective mass within range of a mass measurement accuracy of the respective experimental mass of the spectral peak.

In certain embodiments, determining the first candidate chemical formula is a neutral loss match to the unidentified chemical compound further includes identifying that a stoichiometry of the first candidate chemical formula allows for at least a first candidate neutral molecular composition of the one or more candidate neutral molecular compositions. Identifying that a stoichiometry of the first candidate formula allows for the first candidate neutral molecular composition may include determining, for the first candidate neutral molecular composition, a number of atoms of each type in the first candidate chemical formula is greater than a number of atoms of each corresponding type in the candidate neutral loss composition.

In certain embodiments, identifying the first candidate chemical formula includes: determining at least one of (a) a chemical formula of a repeating structural unit, and (b) an estimated weight of the two or more repeating structural units, where the unidentified chemical compound includes (i) two or more repeating structural units, and (ii) at least one end unit; and identifying the first candidate chemical formula for the unidentified chemical compound based at least in part upon the mass spectrometry data, and based further in part on at least one of (a) the chemical formula of the repeating structural unit, and (b) the estimated weight.

In one aspect, the invention is directed to a system including a processor; and a memory having instructions stored thereon, where the instructions, when executed by the processor, cause the processor to: access mass spectrometry data for a sample including the unidentified chemical compound; identify at least a first candidate chemical formula for the unidentified chemical compound based at least in part on the mass spectrometry data; access spectral data for the first candidate chemical formula; and determine the first candidate chemical formula is a neutral loss match to the unidentified chemical compound. The determining of the neutral loss match may include, for each of a number of spectral peaks of the spectral data: calculating a respective mass difference between a theoretical mass of the first candidate chemical formula and a respective experimental mass corresponding to the spectral peak, and comparing the respective mass difference with a mass of each of one or more corresponding neutral molecular compositions to identify one or more candidate neutral molecular compositions corresponding to the spectral peak.

In one aspect, the invention is directed to a non-transitory computer readable medium having instructions stored thereon, where the instructions, when executed by a processor, cause the processor to: access mass spectrometry data for a sample including the unidentified chemical compound; identify at least a first candidate chemical formula for the unidentified chemical compound based at least in part on the mass spectrometry data; access spectral data for the first candidate chemical formula; and determine the first candidate chemical formula is a neutral loss match to the unidentified chemical compound. The determining of the neutral loss match may include, for each of a number of spectral peaks of the spectral data: calculating a respective mass difference between a theoretical mass of the first candidate chemical formula and a respective experimental mass corresponding to the spectral peak, and comparing the respective mass difference with a mass of each of one or more corresponding neutral molecular compositions to identify one or more candidate neutral molecular compositions corresponding to the spectral peak.

Features of the embodiments described with respect to other aspects of the invention may be used in this aspect of the invention as well.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 3A through 3F are screen shots of an example user interface to a system for identification of polymer species from mass spectrometry output;

FIG. 6 is a block diagram of an example network environment for identification of polymer species from mass spectrometry output;

Figure 1:
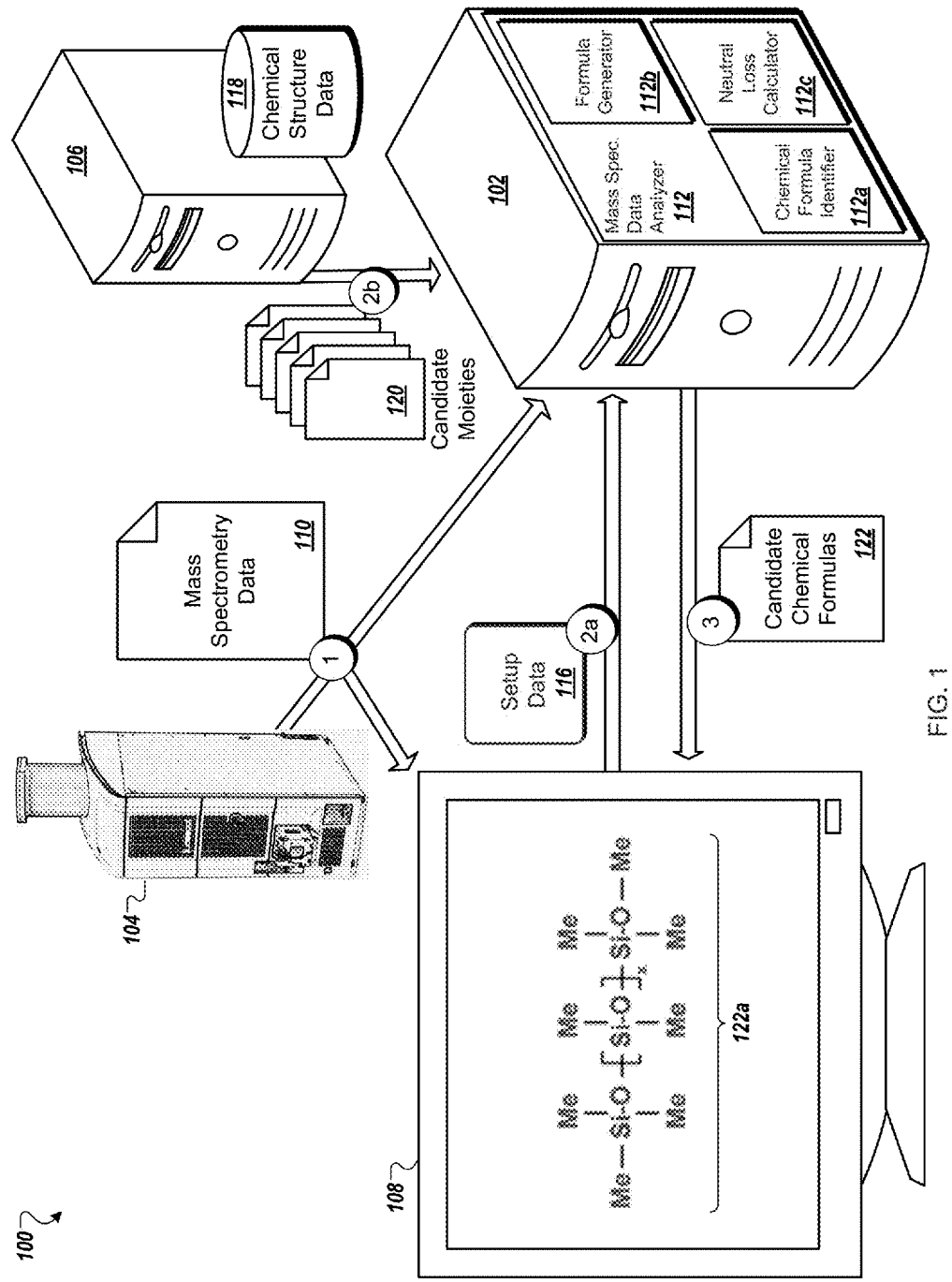
FIG. 1 is a diagram of an example system for identification of chemical formulas from mass spectrometry output.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Throughout the description, where apparatus, devices, and systems are described as having, including, or comprising specific components, or where processes and methods are described as having, including, or comprising specific steps, it is contemplated that, additionally, there are apparatus, devices, and systems of the present invention that consist essentially of, or consist of, the recited components, and that there are processes and methods according to the present invention that consist essentially of, or consist of, the recited steps.

It should be understood that the order of steps or order for performing certain action is immaterial so long as the invention remains operable. Moreover, two or more steps or actions may be conducted simultaneously.

The term "polymer," as used herein, refers to a molecule of high relative molecular mass, the structure of which includes the multiple repetition of units derived, actually or conceptually, from atoms. In some embodiments, a polymer has an average molecular weight greater than about 100 Da. In some embodiments, a polymer has an average molecular weight greater than about 250 Da. In some embodiments, a polymer has an average molecular weight greater than about 500 Da. In some embodiments, a polymer has an average molecular weight greater than about 1,000 Da. In some embodiments, a polymer has an average molecular weight greater than about 10,000 Da.

The term "repeating unit", as used herein, refers to a moiety that occurs at least one time in a polymer molecule. In some embodiments, a repeating unit in a polymer has the same molecular weight as a monomer used to form the polymer.

The term "end group" as used herein, refers to a chemical formula including the polymer molecule, but not within the repeating units. In some embodiments end groups are the end groups of a linear polymer, in other embodiments, the end groups of the current context may represent side chains of a linear or cyclic polymer. End groups can be smaller or larger than repeating units.

As part of establishing a compound's identity using mass spectrometry data, some existing software packages involve referencing established databases when analyzing candidate molecular formulas. For example, Applicant's AxION EC ID (Elemental Composition Identification) software package allows the user to determine the composition of known ("known unknowns") and unknown ("unknown unknowns") compounds from a sample analysis. The program calculates the elemental composition of the analyte based on the measured exact mass of the observed molecular ion and the relative abundance of the isotope ratios in the molecular ion isotopic distribution. AxION EC ID then calculates potential molecular formulas for the analyte, links to the PubChem Compound database, and lists all possible compounds (and associated structures) for that composition.

In certain embodiments, the present invention encompasses the finding that, notwithstanding the excellent results achieved with the existing elemental composition identification software for molecules of relatively low molecular weight (e.g., less than 1000 Da), the ability to efficiently identify molecules of higher molecular weight (e.g., a polymer) is highly desirable. As described herein, the present disclosure provides, among other things, a method including the step of predicting the structure or exact mass of a polymer molecule, wherein the method includes a user input of one or more known repeating units in the polymer molecule. Although the precise identity of the polymer end groups may not be known, the input of one or more known repeating units is sufficient to predict structures or exact masses of parent molecules with a high degree of accuracy.

Any polymeric molecule containing one or more repeating units may be used in accordance with the provided methods. In some embodiments, a polymer analyzed by the provided methods is a homopolymer including only one repeating unit. In some embodiments, a polymer analyzed by the provided methods is a copolymer including two or more different repeating units.

In certain embodiments, a polymer analyzed by the provided methods is selected from the group consisting of a polyglycoside, a polynucleotide, a polypeptide, a polycarbonate, a polyamide, a polyolefin, a polyether, a siloxane, a polyacetal, a polyketal, a polyorthoester, a polyester, a polyaramide, and derivatives thereof.

In certain embodiments, a polymer analyzed by the provided methods is selected from the group consisting of a polysaccharide, a glycopeptide, a glycolipid, and derivatives thereof. In some embodiments, a polymer analyzed by the provided methods is a homopolysaccharide selected from the group consisting of cellulose, amylose, dextran, levan, fucoidan, carraginan, inulin, pectin, amylopectin, glycogen and lixenan. In some embodiments, a polymer analyzed by the provided methods is a heteropolysaccharide selected from the group consisting of agarose, hyluronan, chondroitinsulfate, dermatansulfate, keratansulfate, alginic acid and heparin. In certain embodiments, such polysaccharides may be modified (e.g., bear protecting groups or contain ring-opened units from treatment with oxidizing reagents).

In some embodiments, a polymer analyzed by the provided methods is selected from the group consisting of poly(ethylene carbonate), poly(propylene carbonate), poly(propylene carbonate)-co-poly(ethylene carbonate), poly(butylene carbonate), poly(cyclohexene carbonate), poly(limonene carbonate), and poly(1,2 hexene carbonate).

In some embodiments, a polymer analyzed by the provided methods is a polyamide selected from the group consisting of nylon-6, nylon-6,6, nylon-12, nylon-12,12, and nylon-11.

In some embodiments, a polymer analyzed by the provided methods is selected from the group consisting of a polyethylene, a poly(tetrafluoroethylene), a polypropylene, a polyisobutylene, a polystyrene, a polyacrylonitrile, a poly(vinyl chloride), a poly(methyl acrylate), a poly(methyl methacrylate), a polybutadiene, a polychloroprene, a poly(cis-1,4-isoprene), and a poly(trans-1,4-isoprene).

In some embodiments, a polymer analyzed by the provided methods is selected from the group consisting of poly(lactic acid), thermoplastic starch, poly(3-hydroxybutyrate), poly(4-hydroxybutyrate), poly(3-hydroxy propionate), polyhydroxyoctanoate, poly(3-hydroxyvalerate), poly(3-hydroxybutyrate-co-3-hydroxyvalerate), poly(ethylene terephthalate) (PET), poly(butylene terephthalate), biodegradable polyesters like poly(butylene adipate), poly(ethylene adipate), poly(butylene succinate), poly(butylene adipate-co-terephtalate), poly(butylene adipate-co-butylene succinate), poly(butylene adipate-co-terephtalate), other aliphatic and aromatic polyesters, poly(vinyl alcohol), poly(vinyl acetate), ethylene vinyl alcohol polymer (EVOH), poly (caprolactone), poly(ethylene glycol), poly(propylene glycol), polyoxymethylene, polyether ether ketone, poly(tetramethylene ether) glycol, and polyesteramide.

In some embodiments, a polymer analyzed by the provided methods is a linear polymer. In some embodiments, a polymer analyzed by the provided methods is a cyclic polymer. In some embodiments, a polymer analyzed by the provided methods is a branched polymer. In some embodiments, a polymer analyzed by the provided methods is a globular polymer. In some embodiments, a polymer analyzed by the provided methods is a graft copolymer. In some embodiments, a polymer analyzed by the provided methods is a comb copolymer.

Any repeating unit of a polymer can be used in accordance with the provided methods. In some embodiments, such a repeating unit is contained in a polymer described above. In certain embodiments, repeating units are the smallest possible units of monomers that form a polymer. For example, a repeating unit of polydimethylsiloxane is —$Si(CH_3)_2O$—. In certain embodiments, a repeating unit can include two or more monomeric units, such as in the copolymer polyethylene carbonate where a repeating unit can be —$OC(O)O(CH_2)_2$—, or the repeating unit may be further broken into monomers —$OC(O)$— and —$O(CH_2)_2$—.

In some implementations, the present disclosure may be directed to a system and method for identification of polymer species from mass spectrometry output. To aid in the speed and accuracy of identification of a chemical compound including a unit that repeats one or more times, such as a polymer structure, a software tool for chemical formula identification may be provided with one or more candidate repeating units as an input. In some implementations, the software tool may be used to identify polymeric species having a repeating unit that repeats at least three times. Using the repeating units, the software tool may iteratively search for a chemical formula including the repeating units plus an end unit structure matching the mass spectrometry output within a threshold tolerance.

In some implementations, the software tool accepts both a repeating unit structure and a limitation upon the structure of one or both end unit(s). For example, a user may limit the number of elements composing each end unit to a maximum number of elements (e.g., 10). In another example, a user may limit the type of elements to a particular set.

The present disclosure, in some implementations, may be directed to a system and method for identification of a chemical formula of a sample compound based at least in part upon the neutral loss. Herein, neutral loss refers to a mass difference between two mass spectral peaks due to processing such as front-end chemistry or gas-phase fragmentation which results in a loss of molecular formula. The loss of molecular formula can be attributed to at least one existing and reported neutral, stable molecule. A majority of gas phase collisionally induced disassociation reactions, for example which proceed via a unimolecular decay slightly above the apparent activation barrier on a kinetic scale of time-of-flight (TOF) mass spectrometry with ion activation in the ion guide or in the ion source, will demonstrate neutral loss. In these reactions, for example, the mass difference between the product and a reactant equals a mass of some known (e.g., reported and stored in a chemical formula database) neutral molecule. In determining a degree of matching between a candidate chemical formula and features of a chemical formula identified through mass spectrometry data, a neutral loss analyzer compares, for each spectral peak within the mass spectrometry data, observed mass difference (e.g., between a spectral peak and an adjacent spectral peak) with mass molecular compositions within a database of chemical formulas. The method of neutral loss analysis, for example, may increase accuracy or narrow a pool of potential candidates of chemical formulas in relation to the following examples: collision-induced disassociation in capillary-skimmer region of a TOF mass spectrometer; metabolites in bulk; front-end chemical reactions (e.g., reactions in a sample prior to mass spectrometry); and polymer identity in relation to exact mass of the repeating unit.

Turning to FIG. 1, an example system 100 for identification of chemical formulas from mass spectrometry output is illustrated. The system 100 includes a spectrometry data analysis server 102 configured to analyze a set of mass spectrometry data 110 generated by a mass spectrometer 104 to identify one or more chemical formulas based upon a comparison of information derived from the mass spectrometry data 110 to information contained within a chemical formula data store 106. A user may interface with the spectrometry data analysis server 102 via a computing device 108 (e.g., a computing device locally or remotely connected to the data analysis server 102 or input/output (I/O) peripheral devices connected directly to the spectrometry data analysis server 102).

In some implementations, a user operating the computing device 108 accesses a mass spectrometry data analyzer 112 executing upon the spectrometry data analysis server 102. In some implementations, the user supplies the mass spectrometry data 110 generated by the mass spectrometer 104 to the mass spectrometry data analyzer 112. The user, in other implementations, selects the mass spectrometry data 110 from available mass spectrometry data (e.g., previously downloaded, transferred, or otherwise made available to the data analysis server 102 by the mass spectrometer 104). In some implementations, the mass spectrometer 104 includes the data analysis server. For example, the data analysis server 102 may be implemented as one or more computer processors functioning within a mass spectrometer system.

In some implementations, the mass spectrometry data analyzer 110 calculates additional data from the mass spectrometry data 110. For example, based upon the experimental information contained within the mass spectrometry data 110, a mass-charge ratio of ions (e.g., calculated as centroids of the peaks in the so-called "profile" spectra), the relative intensities of the peaks, and/or electric charge (e.g., based on relative position of peaks believed to be representing the same isotope cluster).

In addition to the mass spectrometry data 110, in some implementations, the user supplies the mass spectrometry data analyzer 112 with setup data 116. The setup data 116, in some examples, includes the selection of one or more functions of the mass spectrometry data analyzer 112 such as, in some examples, a chemical formula identifier 112a, a formula generator 112b, and a neutral loss calculator 112c.

The chemical formula identifier 112a, for example, may analyze the mass spectrometry data 110 to determine one or more chemical formulas that include spectrometry features similar to (e.g., within a threshold distance from) features of the mass spectrometry data 110. The setup data 116 provided to the chemical formula identifier 112a may include, in some examples, accurate mass of the monoisotopic peak, a charge carrier, isotope abundances, and/or a database of chemical formulas for identifying candidate chemical formulas. A user may provide, for example through importing mass spectrometry data or by inputting data by hand, an accurate mass of the monoisotopic peak. The accurate mass of the monoisotopic peak, for example, may be taken as a centroid of the profile peak of the mass spectrometry output. Based upon the mass spectrometry output, in some implementations, a default charge carrier may be selected. In other implementations, the user may select a charge carrier (for example, based upon experimental data or the anticipated content of the experimental chemical compound). Isotope abundances (e.g., relative or absolute intensities of respective peaks in the spectrum), in some implementations, are imported by the chemical formula identifier 112a from the mass spectrometry data 110. A chemical formula database, in some examples, may include the PubChem Compound database maintained by the National Center for Biotechnology Information (NCBI) or the molecular spectral databases maintained by the National Institute of Standards and Technology (NIST). In some implementations, the mass spectrometry data analyzer 112 may set a default chemical formula database (e.g., a built-in database or a particular public database).

In some implementations, a threshold variance setting limits the number of candidate chemical formulas. The user, in some implementations, may set a parts-per-million (ppM) error cutoff. In some examples, the ppM error cutoff may be set as 20 ppM, 10 ppM, 5 ppM, or 3 ppM. In some implementations, the ppM cutoff is selected based upon the type of mass spectrometry analysis performed. For example, for a time-of-flight mass spectrometer, a reasonable ppM cutoff of 3 ppM may be entered. In some implementations, the chemical formula identifier 112a determines the ppM cutoff, for example based upon information contained within the mass spectrometry data 110. In other implementations, the user may set the ppM cutoff error.

The chemical formula identifier 112a, in some implementations, iteratively searches chemical formulas to identify a structure including similar data (e.g., relative atomic mass, similar total number of isotopes, similar relative intensity of isotopes, etc.) to the mass spectrometry data 110. The setup data provided to the chemical formula identifier 112a, for example, may include a subset of elements, where any candidate chemical formulas are limited to those composed of the subset of elements. Instead of or in addition to the subset of elements, in another example, the setup data 116 may include a maximum number of elements, where candidate chemical formulas are limited to those composed of a total number of elements less than or equal to the maximum number of elements. In a further example, the setup data 116 may include a candidate charge carrier for the chemical formula.

The chemical formula identifier 112a identifies one or more candidate chemical formulas, in some implementations, based upon a mass of an experimental compound (e.g., as determined from the mass spectrometry data 110) and a predetermined set of elements (e.g., C, H, F, O, N, Si, etc.). Using this information, for example, the mass of a candidate chemical formula can be calculated as a sum of the atomic masses of a subset of the predetermined set elements, where each of the subset of elements may be included within the candidate chemical formula one or more times. In some implementations, nested loops of summations are used to iterate through all possible combinations of elements in order to identify combinations having a mass within a threshold distance of the mass of the experimental compound.

In some implementations, the setup data 116 may include a candidate moiety. The candidate moiety, in some implementations, is selected by the user from a set of candidate moieties 120, for example, derived from chemical formula data 118 retrieved from the chemical formula data store 106. The chemical formula data store 106, for example, may include a database such as the PubChem Compound database maintained by the National Center for Biotechnology Information (NCBI), containing about 26 million chemical compounds and 1.3 million unique molecular formulas. In another example, the chemical formula data store 106 may include a database such as the molecular spectral databases maintained by the National Institute of Standards and Technology (NIST). In other implementations, the user inputs (e.g., types in, draws a chemical formula, drags and drops a chemical formula, etc.) a candidate chemical moiety.

The candidate moiety, in some implementations, is designated by the user as a repeating unit for a chemical formula composed of a repeating unit plus end units. The repeating unit, for example, may be a repeating unit of a known polymer. In response to identifying the mass spectrometry data 110 as including repeating units (e.g., in setup data 116 or previous data provided by the user of the computing device 108), in some implementations, candidate moieties 120 may be derived based upon estimated molecular weights of the repeating unit. For example, knowing that the sample includes a polymeric species with a repeating unit, a relative mass of a repeating unit portion of the polymeric species may be estimated from the mass spectrometry data. In a particular example, the mass spectrometer output includes a spectral pattern characteristic of a polymer with a repeating unit with a molecular mass of approximately 76 dalton (Da). A manual or partially automated identification method may be used to match the molecular mass of 76 Da to the candidate repeating unit of polydimethylsiloxanes (e.g., $C2H6SiO$).

In the circumstance of the candidate moiety identifying a repeating unit, in some implementations, the formula generator 112b may be invoked to determine one or more matching chemical formulas including the candidate repeating unit plus an end unit structure. The user, in some implementations, is provided the opportunity to limit the chemical formula of the end unit, for example to increase the speed and/or accuracy of chemical formulas identified by the software tool. In one example, the user limits the end unit to a maximum number of chemical elements (e.g., as designated by the setup data 116). In some implementations, the formula generator 112b assumes an identical chemical composition of each end unit. In other implementations, the chemical composition of each end unit may vary.

The formula generator 112b determines one or more candidate chemical formulas 122 (e.g., candidate polymer structures) based in part upon the candidate moiety 120. Similar to the functionality of the chemical formula identifier 112a, the formula generator 112b identifies one or more candidate chemical formulas, in some implementations, based upon a mass of an experimental compound (e.g., as determined from the mass spectrometry data 110) and a pre-determined set of elements (e.g., C, H, F, O, N, Si, etc.). However, because a large portion of the mass of the experimental compound is immediately accounted for based upon the candidate moiety 120, only the composition of the each of the end groups of the experimental chemical formula needs to be determined. In some implementations, the user identifies an estimated number of iterations of the candidate moiety 120 included within the experimental chemical compound. In other implementations, the formula generator 112b determines a default number of iterations of the candidate moiety 120 (e.g., the maximum number of iterations of the mass of the candidate moiety 120 that does not exceed the mass of the experimental chemical compound, as determined via the mass spectrometry data 110). In some implementations, rather than identifying a candidate moiety, the formula generator 112b is provided an estimated mass of the repeating unit or total mass of the repeating unit (e.g., including all iterations involved within the experimental chemical compound). Either way, based upon the provided information, the formula generator 112b may begin the identification process with a "super atom" of a known mass.

Additionally, because the formula generator 112b is identifying potential end group combinations built upon the candidate moiety 120, the maximum number of each type of element in the predetermined set of elements may be greatly reduced in comparison to the algorithm used by the chemical formula identifier 112a. For example, the end groups of large biomolecules, such as polymers, may be assumed to contain no greater than X number of each of the predetermined set of chemical elements, where X may vary from element to element based upon known chemistry. In some implementations, the user is provided the opportunity to set a maximum number of each chemical element to include within the end groups of the candidate chemical formulas. The maximum number of each element of the predetermined set of elements, in some implementations, may be identified as a default setting within the formula generator 112b.

In some implementations, in addition to or instead of determining candidate chemical formulas based upon a repeating unit, the mass spectrometry data analyzer 112 is configured to identify one or more candidate chemical formulas based upon a neutral loss estimate. The neutral loss calculator 112c, in some implementations, may analyze a candidate chemical formula in view of the mass spectrometry data 110 to identify a potential match based upon a neutral loss theory. Herein, neutral loss refers to a mass difference between two mass spectral peaks due to processing such as front-end chemistry or gas-phase fragmentation which results with a loss of molecular formula. The loss of molecular formula can be attributed to at least one existing and reported neutral, stable molecule. The neutral loss calculator 112c, in some implementations, receives one or more candidate chemical formulas from the chemical formula identifier 112a or the formula generator 112b. For example, the neutral loss calculator 112c may be used to refine resultant candidate chemical formulas. In analyzing candidate chemical formulas based upon neutral loss calculations, for example, an initial list of candidate chemical formulas may be narrowed to provide more accurate results and/or re-prioritized to promote a candidate chemical formula best matching the mass spectrometry data 110 in relation to the neutral loss concept.

The neutral loss calculator 112c analyzes the candidate chemical formula (s) for a potential match with the mass spectrometry data 110 based upon the mass difference in principle between any two mass spectral peaks. In some implementations, the neutral loss calculator receives one or more candidate chemical formulas from the chemical formula identifier 112a or the formula generator 112b. The user, in some implementations, selects a candidate chemical formula for neutral loss calculation. The candidate chemical formula, in some examples, may be selected from a results list provided via the chemical formula identifier 112a or the formula generator 112b, through selecting a chemical formula from a database, and/or by manually entering a candidate chemical formula.

Beginning with the experimental compound (e.g., as identified within the mass spectrometry data 110) and a particular candidate chemical formula, the neutral loss calculator 112c, in some implementations, identifies spectral data associated with the candidate chemical formula. The spectral data, for example, may be obtained through the chemical structure data 118. The neutral loss calculator 112c, in some implementations, searches the peak list of the spectrum included within the mass spectrometry data 110, calculating mass difference between the theoretical mass of the candidate chemical formula spectrum and experimental mass of all other spectral peaks obtained from the mass spectrometry data 110. For each spectral peak, for example, the neutral loss calculator 112c may compare the difference (e.g., calculated between the candidate chemical formula spectrum and the observed mass obtained from the mass spectrometry data 110) with masses of known molecular compositions. The molecular compositions, for example, may be identified as neutral molecular compositions. The molecular compositions, in some implementations, are obtained from a database such as the PubChem Compound database maintained by NCBI or the molecular spectral databases maintained by NIST. The user, in some implementations, provides a list of neutral molecular compositions or narrows an initial list of neutral molecular compositions.

As a result of the comparison implemented by the neutral loss calculator 112c, in some implementations, one or more potential neutral loss matches may be identified. Identification of a neutral loss match, for example, may be based upon the difference between the experimental neutral loss and theoretical mass of a particular molecular composition being less than a mass measurement accuracy threshold. The mass measurement accuracy threshold, for example, may include a default setting or a setting supplied by a user. Additionally, in some implementations, the neutral loss calculator 112c may determine that the stoichiometry of the particular molecular composition allows for a proposed neutral loss candidate. This determination, for example, may be based upon the number of elements of each type of element composing the particular molecular composition being less than or equal to a number of atoms of this type of element occurring in the candidate chemical formula.

In some implementations, instead of attempting to make an assignment of chemical formula candidates to all spectral peaks in the peak list, the neutral loss calculator 112c attempts to assign neutral losses to mass difference between a particular molecular composition and observed (potential) fragments.

Upon identifying one or more candidate chemical formulas 122, in some implementations, the mass spectrometry data analyzer 112 presents the candidate chemical formulas 122 to the user. For example, the user may be provided a series of selectable chemical formulas, such as a first polymer structure 122a, within a graphical user interface of the computing device 108. In addition to a listing of chemical formulas, in some implementations, the mass spectrometry data analyzer 112 provides a numeric and/or graphical comparison of the mass spectrometry data to mass spectrometry values of the candidate chemical formulas. Upon selecting one of the candidate chemical formulas, for example, data related to the selected chemical formula may be overlaid upon a graphical analysis of the mass spectrometry data. Metrics, in another example, may be presented to the user, illustrating a margin of error between spectral features of the mass spectrometry data 110 and the candidate chemical formulas 122. Example user interfaces for providing the setup data 116 and reviewing the candidate chemical formulas 122 are illustrated in relation to FIGS. 3A through 3F.

Figure 2A:
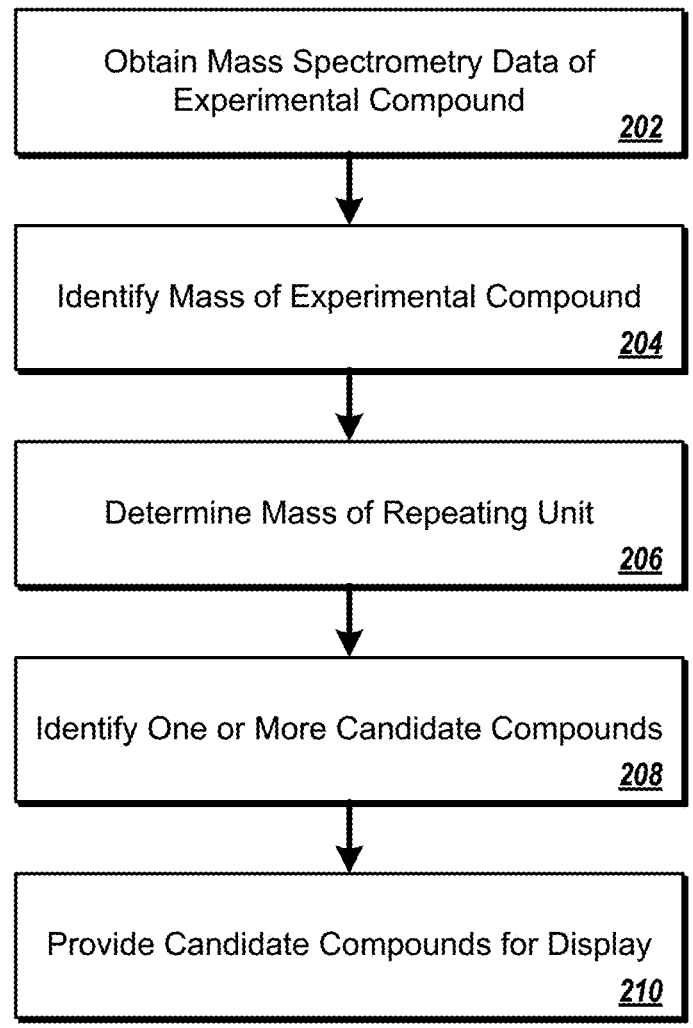
FIGS. 2A through 2C are flow charts of example methods for identification of polymer species from mass spectrometry output.
Figure 2B:
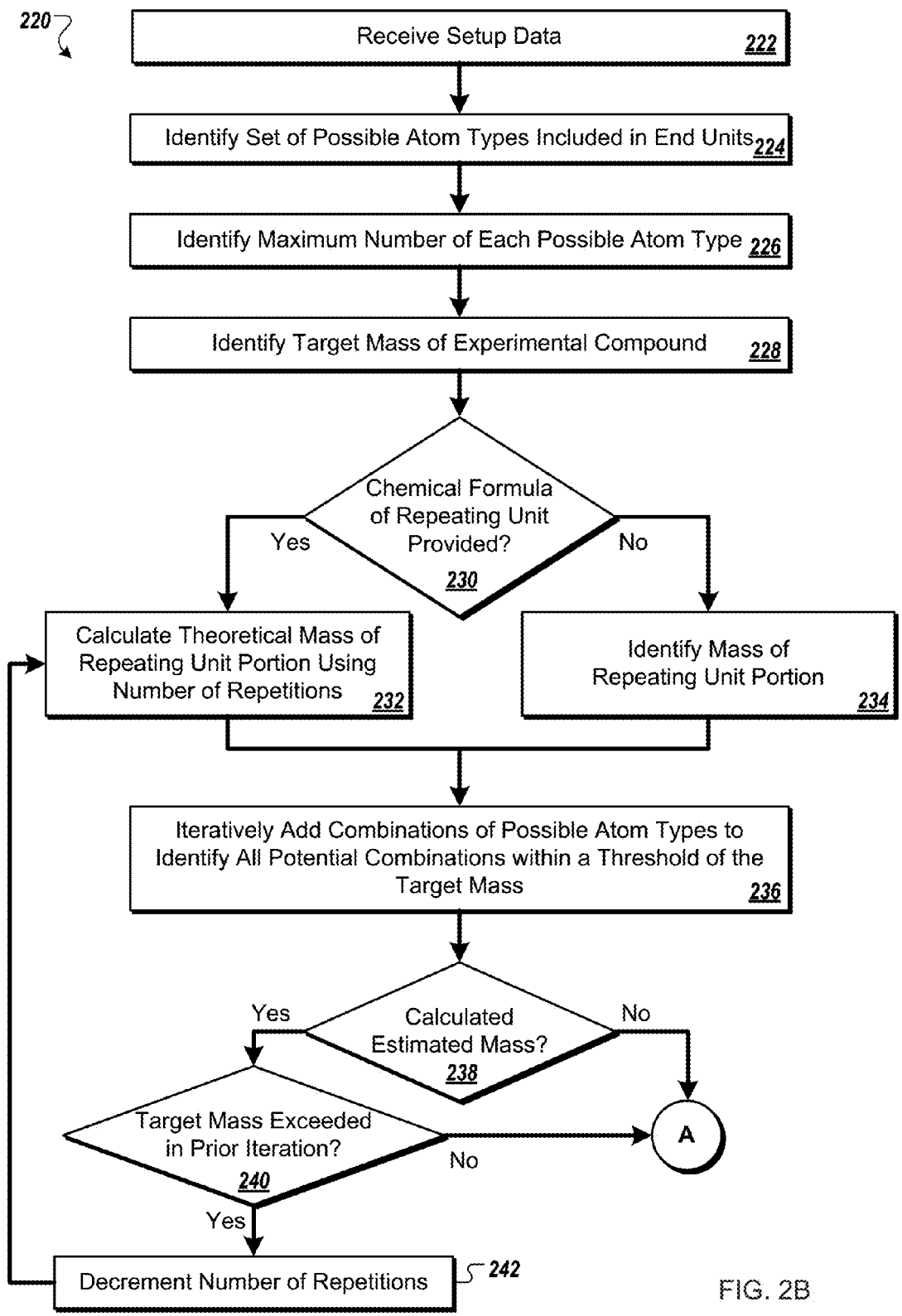
Figure 2C:
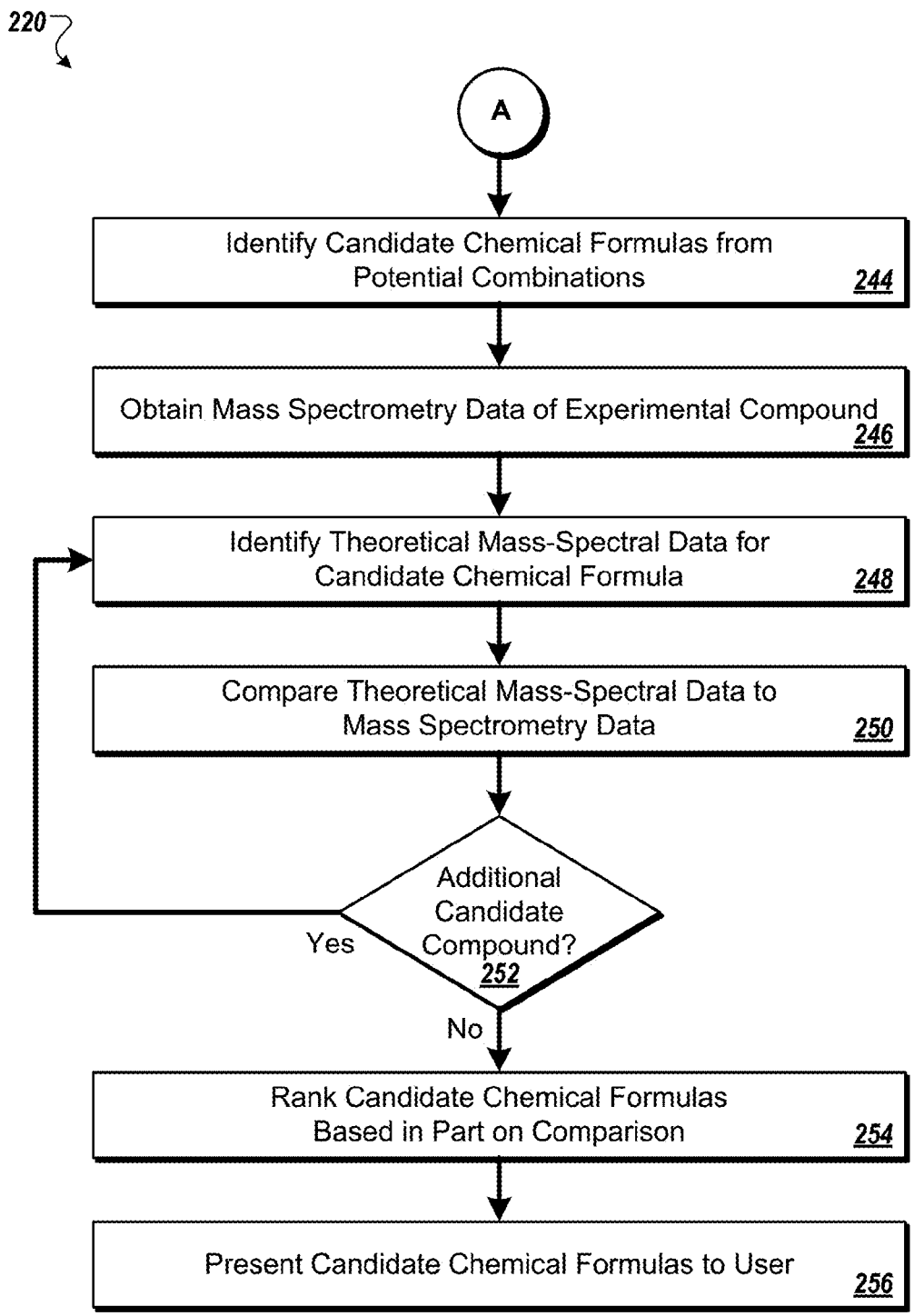

FIGS. 2A through 2C are flow charts of example methods for identification of polymer species from mass spectrometry output. In some implementations, the example methods may be performed by the formula generator 112b, described in relation to FIG. 1.

Turning to FIG. 2A, a first method 200 for identification of polymer species from mass spectrometry output involves determining one or more candidate compounds based in part upon a mass of a repeating unit portion of an experimental polymer compound.

In some implementations, the method 200 begins with obtaining mass spectrometry data of the experimental compound (202).

In some implementations, a mass of the experimental compound is identified (204).

In some implementations, a mass of the repeating unit is determined (206).

In some implementations, one or more candidate compounds are identified (208).

In some implementations, the one or more candidate compounds are provided for display to a user (210).

Although the method 200 is illustrated as a particular series of steps, in some implementations, more or fewer steps may be included. Furthermore, in some implementations, one or more of the steps may be executed in a different order than described above. Other modifications are possible without diverging from the spirit and scope of the method 200.

Turning to FIGS. 2B and 2C, a second method 220 for identification of polymer species from mass spectrometry output involves identifying possible atom types for the end units of the polymer and calculating combinations of atoms to identify candidate polymer formulas within a threshold distance of an experimental mass of the experimental chemical compound.

In some implementations, the method 220 begins with receiving setup data (222).

In some implementations, a set of possible atom types included in the end units of candidate chemical formulas are identified (224).

In some implementations, a maximum number associated with each atom type of the set of possible atom types is identified (226).

In some implementations, a target mass of the experimental chemical compound is identified (228).

If a chemical formula of a repeating unit is provided as input to the method 220 (230), in some implementations, a theoretical mass of the repeating unit portion is calculated (232). The calculation, in some implementations, may involve multiplying the mass of the repeating unit by a number of iterations of the repeating unit. If a number of repetitions was not specified as input, in some implementations, the method 220 may identify an initial number of repetitions.

If a chemical formula of the repeating unit has not been provided (230), a mass of the repeating unit portion is identified (234). In this circumstance, the mass of the repeating unit portion identifies a total mass of the repeating unit, including all repetitions of the repeating unit.

In some implementations, combinations of possible atom types are iteratively summed in order to identify all potential combinations of end types with a total mass (including the mass of the repeating unit portion), within a threshold of the target mass of the experimental compound (236).

In some implementations, if the estimated mass of the repeating unit was initially calculated based upon a provided chemical formula (238), and the target mass of the experimental compound was exceeded in one or more of the iterations (240), a number of repetitions of the target chemical formula of the repeating unit is decremented (242).

The method 220, at this point, returns to calculating the theoretical mass of the repeating unit portion using the reduced number of repetitions (232). For example, if, in the first loop, the theoretical mass of the repeating unit portion was calculated using seven instances of the repeating unit chemical formula mass, the second loop will involve calculating the theoretical mass based upon six instances of the repeating unit chemical formula mass.

Turning to FIG. 2C, upon completion of all iterations, in some implementations, candidate chemical formulas are identified from the set of potential combinations (244).

In some implementations, mass spectrometry data of the experimental compound is obtained (246).

In some implementations, theoretical mass-spectral data for a candidate chemical formula is identified (248).

In some implementations, the theoretical mass-spectral data of the candidate chemical formula is compared to the mass spectrometry data (250).

If additional candidate compounds were identified (252), for each candidate chemical compound, steps (248) and (250) are repeated.

In some implementations, the candidate chemical formulas are ranked based at least in part upon the comparison (254).

In some implementations, the candidate chemical formulas are presented to a user (256).

Although the method 220 is illustrated as a particular series of steps, in some implementations, more or fewer steps may be included. Furthermore, in some implementations, one or more of the steps may be executed in a different order than described above. Other modifications are possible without diverging from the spirit and scope of the method 220.

FIGS. 3A through 3F are screen shots of an example user interface to a system for identification of polymer species from mass spectrometry output. The screen shots depict a series of user interactions involving matching an experimental chemical formula known to be a polymer containing the repeating unit $C_2H_6SiO$.

The repeating unit $C_2H_6SiO$, in some examples, may be selected by a user (e.g., from a list of common chemical formulas provided by the program for selection or a list of user-specific chemical formulas input into the system previously by the user, etc.), dragged and dropped by a user from a separate module, or entered by the user (e.g., in a text entry control). In some implementations, rather than entering the chemical formula of a repeating unit, the user has the option of entering a mass of the repeating unit. The entry method of the repeating unit may vary depending upon the circumstances. For example, in many cases, such as analytical studies of synthetic products, a researcher has sufficient knowledge of the sample history (e.g., synthesis design) to simply use the program to verify that the anticipated polymer was built or to determine the composition of the end units of a known (or suspected) polymeric repeating unit.

Figure 3A:
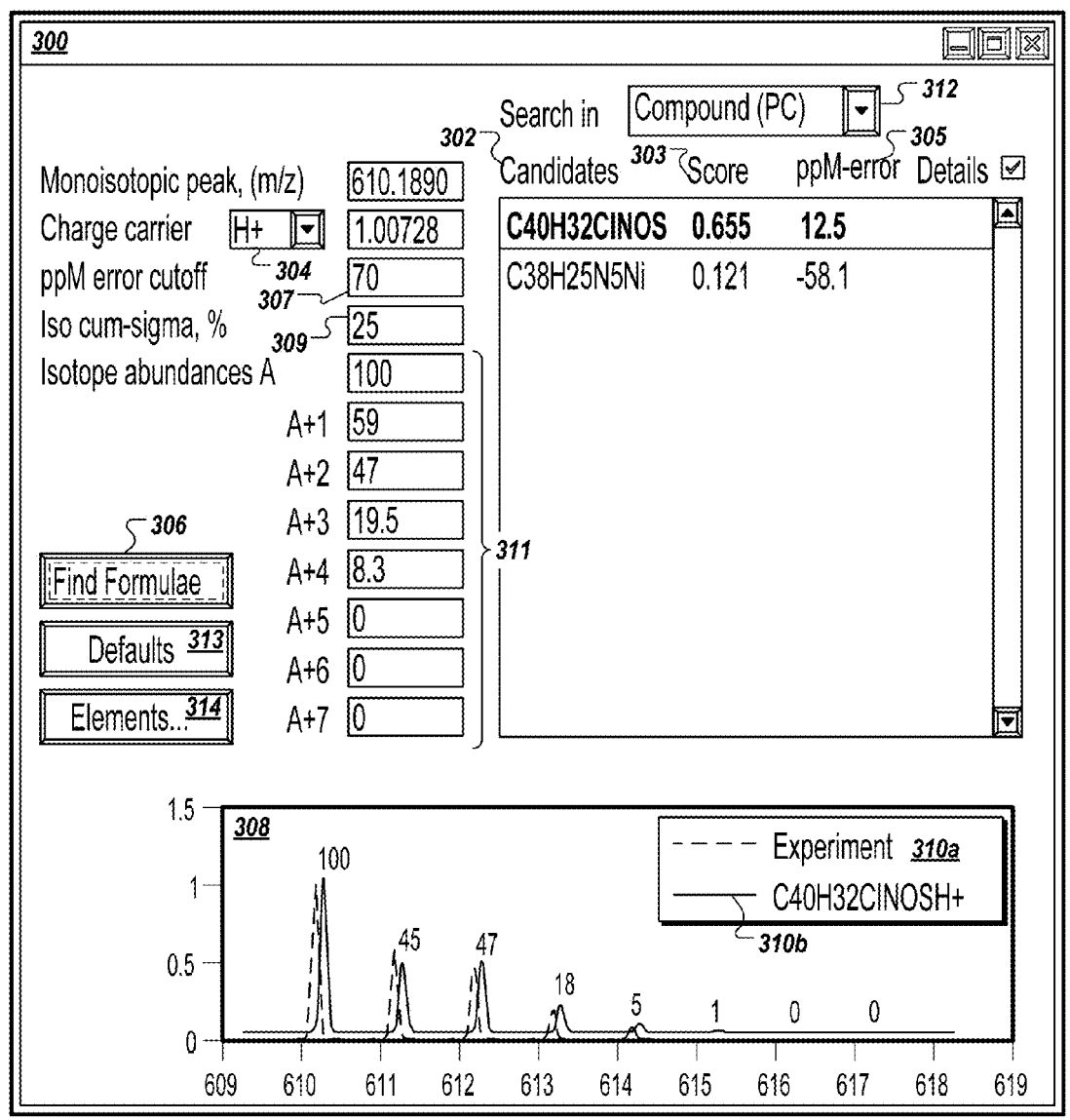
Figure 3B:
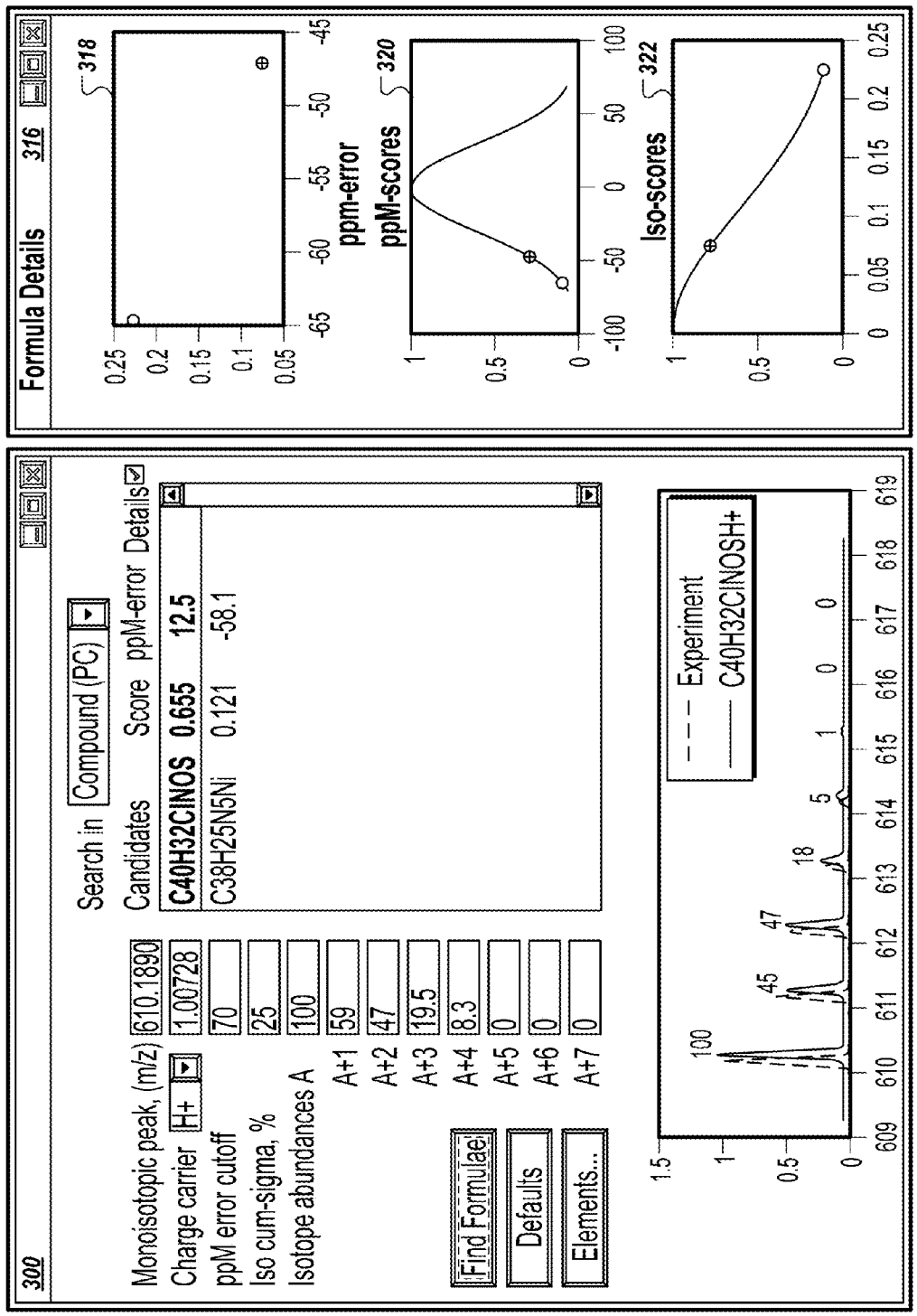

Turning to FIG. 3A, a main window 300 illustrates a first set of candidate chemical formulas 302. The first set of candidate chemical formulas 302 were initially selected by setting a charge carrier 304 of a proton (H+) and selecting a "Find Formulae" control 306. For example, the first set of candidate chemical formulas 302 may have been derived using the chemical formula identifier 112a as described in relation to FIG. 1. Each candidate formula 302 of the first set of candidate chemical formulas 302, in some implementations, is identified based upon a mass $M_{experimental}$ of the experimental compound and a pre-determined set of a number K of elements (e.g., C, H, F, O, N, Si, etc.). In some implementations, the user may specify the pre-determined set of K elements. For example, through selection of an elements control 314, an element selection interface may be presented to the user to identify a subset of chemical elements to include in candidate chemical formulas. For example, selection of the elements control 314 may result in presentation of a graphical representation of a periodic table. Through selecting individual elements, the user may allow and/or disallow particular elements from being included within the candidate chemical formulas.

Using the mass of the experimental compound and the pre-determined set of K elements, for example, the mass $M_i$ of a candidate molecule can be calculated as a sum of the atomic masses of a subset of the K elements multiplied individually by a number $n_k$ of elements of each type (e.g., C, H, F, O, N, Si, etc.) In some implementations, nested loops of summations (e.g., n=0, 1, . . . N, k=0, 1, . . . K) are used to iterate through all possible combinations of elements in order to identify combinations having a mass within a threshold distance of the mass $M_{experimental}$. Various algorithmic implementations may involve, in some examples, hard loops, recursion, and/or sorting by atom-type mass before determining iterative structure.

In some implementations, the algorithm may involve a number of rules and/or limitations, for example based on general chemistry, to restrict the number of iterations involved in the candidate chemical formula selection. For example, the set of K elements may be restricted to certain elements or element types. In another example, one element type may be related to another element type (e.g., if element X is used, do not consider chemical formulas involving element Y, or vice-versa).

Regardless the particular implementation of the chemical formula candidate identification algorithm, the iterative approach of identifying candidates based upon the mass $M_{experimental}$ of the experimental compound and the pre-determined set of a number K of elements inherently suffers from exponential nature of dependence of computational steps involved on (1) the target ion, and (2) the number of atom types allowed for consideration. The resultant candidate formulas illustrated within FIG. 3A illustrate the limitations of this approach for candidate formula identification. The first set of candidate chemical formulas 302, for example, where selected from the "Compound (PC)" database, as selected within a chemical formula database drop-down menu 312. The first set of candidate chemical formulas 302 contain a first candidate chemical formula 302a of $C40H32ClNOS$ and a second candidate chemical formula 302b of $C38H25N5Ni$. As can been seen by the first set of candidate chemical formulas 302, neither candidate chemical formula 302 contains the repeating unit of the polymer (e.g., $C_2H_6SiO$). Thus, FIG. 3A illustrates the potential for error when attempting to determine a large mass polymer using a strictly iterative matching solution.

The candidate chemical formulas 302, in some implementations, may be displayed in a ranked order, for example based upon a closest similarity between the spectral pattern, mass, and other information within the mass spectrometry data of the experimental chemical formula and data regarding each candidate chemical formula, for example as supplied by the database elected within the drop-down menu 312. Each candidate chemical formula 302, as illustrated, is associated with a respective score 303 and a respective parts-per-million error (ppM-error) 305. The ppM-error 305, for example, may be determined based upon a comparison of user-specified experimentally observed mass of the monoisotopic peak to the candidate chemical formula mass data (e.g., as obtained from a chemical formula database). In some implementations, the ppM-error 305, upon calculation, may then be used by the system (e.g., the mass spectrometry data analyzer 112 described in relation to FIG. 1) to narrow the resultant candidates. For example, for each candidate chemical formula having a ppM-error 305 outside a ppM error cutoff 307 may be discarded from the results list.

The respective score 303, in some implementations, is calculated in a manner to separate the valuation of the candidate from dependence upon data provided by a particular database. For example, the respective score 303 may initially be based upon an experimentally observed mass of the monoisotopic peak in view of a mass accuracy cutoff (e.g., as set by the system by default or as provided by the user, for example within a ppM error cutoff field 307 of the main window 300), in a mass error distribution function scaled to unity. The respective score 303, in other words, will have a value of one to indicate a perfect match between experimental data and a candidate chemical formula. A candidate chemical formula with a mass residual other than zero, in this example, will be awarded a respective score 303 that is less than one.

In some implementations, the respective score 303 is further refined by constructing a second scoring value relative to isotope abundances. A cumulative absolute error cutoff (e.g., a default value provided by the system or a value specified by the user within an iso cum-sigma data field 309), for example, may used as a sigma-parameter of a one-sided unity-scaled zero-centered normal distribution. The difference in relative isotope abundances, when taken in view of the distribution, may provide a relative measure matching between theoretically calculated relative abundance of isotopes of a candidate molecular formula and the experimental relative abundance of isotopes. In combining both the mass-based scoring value and the isotope-abundance based scoring value, in some implementations, the respective score 303 is obtained. For example, the two values may be treated as orthogonal coordinates to calculate the final score, as a Euclidian distance scaled to unity.

In some implementations, selection of a defaults control 313 may result in setting one or more of a default charge carrier, a default ppM error cutoff 307, and/or a default iso cum-sigma percentage 309.

In a graphical comparison pane 308, an experimental spectral pattern 310a is overlaid with a candidate pattern 310b. The candidate pattern 310b, for example, illustrates a spectral pattern of a first candidate chemical formula 302a of C40H32ClNOS (e.g., illustrated as highlighted above within the list of candidate chemical formulas 302).

In some implementations, values of the experimental spectral pattern 310a relate to a set of isotope abundances 311 illustrated above the graphical comparison pane 308. The isotope abundances 311, in some implementations, may be automatically identified, for example based upon mass spectrometry data provided to the system. For example, for each isotopic peak within a provided spectrum, the system (e.g., mass spectrometry analyzer 112 as described in relation to FIG. 1) may import a respective isotope abundance 311. The user, in some implementations, may be provided the opportunity to manually enter or manually adjust the isotope abundances 311.

In addition to the graphic illustration provided within the graphical comparison pane 308, in some implementations, detailed information regarding the experimental spectral pattern 310a in comparison to the candidate pattern 310b of C40H32ClNOS is provided. For example, turning to FIG. 3B, a formula statistics window 316 is presented next to the main window 300. The formula statistics window 316 provides an absolute error distance graph 318, a ppM-scores graph 320, and an iso-scores graph 322. As discussed above in relation to the scores 303 of FIG. 3A, the scores 303, in some implementations, illustrate a combination of a mass error score and an isotope abundance error score. For example, the absolute error distance graph 318 may illustrate a relative value of a first portion (e.g., isotope error) of the score 303a, while the ppM-scores graph 320 may illustrate the relative value of a second portion (e.g., mass error) of the score 303a. The iso-scores graph 322, in this example, may illustrate a graphical representation of the score 303a (e.g., 0.655).

Figure 3C:
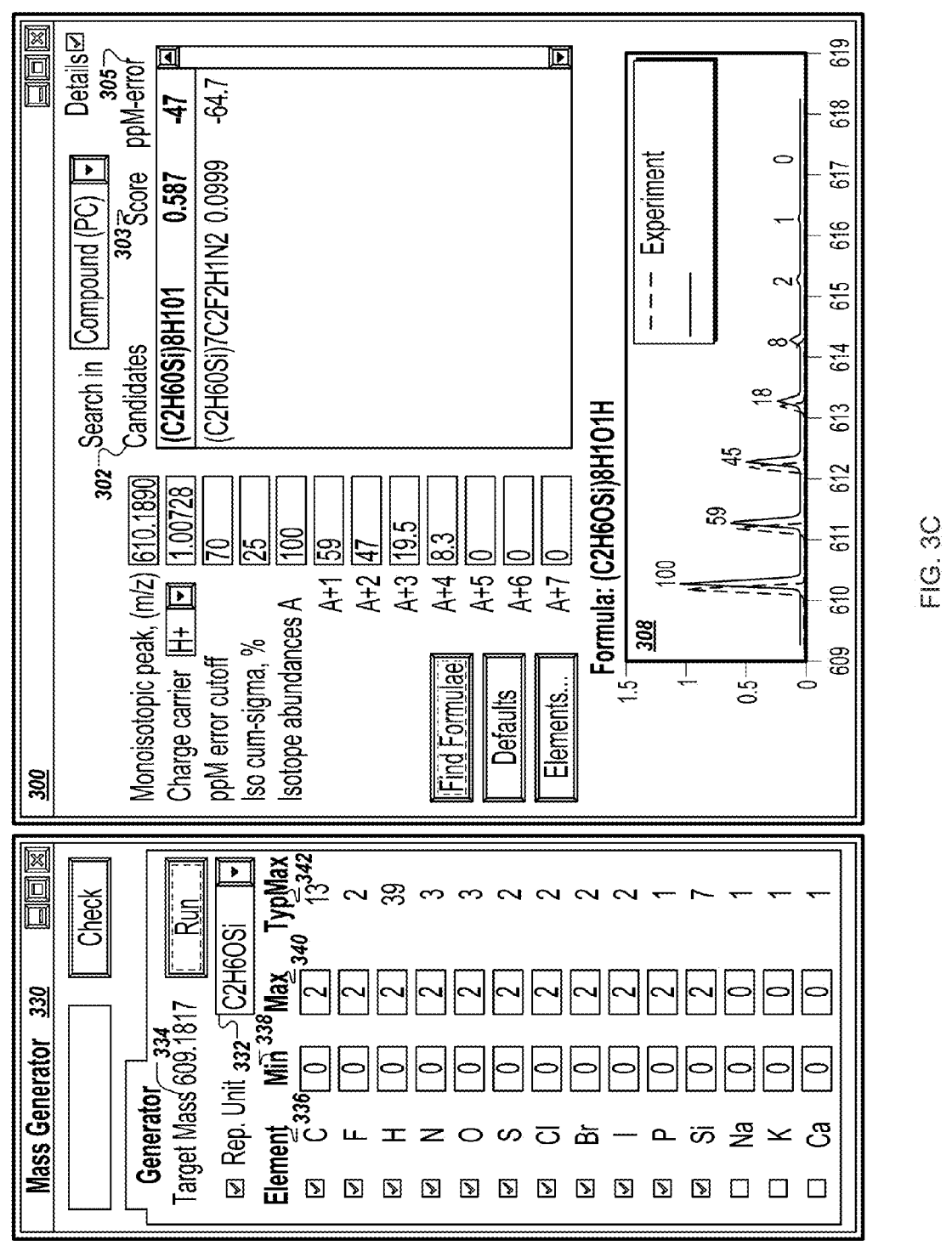

Turning to FIG. 3C, a formula generator window 330, in some implementations, is used to supply setup data regarding a chemical formula involving a repeating unit plus end units. The formula generator window 300, for example, may be used to provide setup data 116 to the formula generator 112b, as described in relation to FIG. 1. The formula generator window 330 includes a drop-down menu 332 for selecting a repeating unit. The contents of the drop-down menu 332, for example, may be selected based in part upon a target mass of the repeating unit, such as a target mass 334 illustrated above the drop-down menu 332. In some implementations, the target mass 334 is derived from the mass spectrometry data regarding the experimental chemical formula. Although illustrated as a drop-down menu 332, in some implementations, a user has the option of manually entering the chemical formula of the repeating unit.

Beneath the drop-down menu 332, a series of chemical elements 334 is illustrated, including a minimum number 338, a maximum number 340, and a TypMax 342. The minimum number 338 and the maximum number 340 may be set to specify a range of the numbers of each element that an end unit of the experimental chemical formula may contain. For example, the user has selected that the end unit may contain between 0 and 2 of each of the following elements: carbon 336a, fluorine 336b, hydrogen 336c, nitrogen 336d, oxygen 336e, sulfur 336f, chlorine 336g, bromine 336h, iodine 336i, phosphorus 336j, and silicon 336k. The following elements have not been selected, and thus may not be included within either end unit: sodium 336l, potassium 336m, and calcium 336n. The values illustrated within the TypMax 342 column, in some implementations, identify typical maximum values for each chemical element, for example derived through chemistry-based restrictions (e.g., limitations derived via chemistry literature regarding the composition of the end units of known polymer compounds). The TypMax 342 values, for example, may be used as a guide by the user when identifying a maximum number related to each chemical element.

As illustrated, based upon the settings within the formula generator window 330, the main window 300 contains a new set of candidate chemical formulas 302, including a first candidate chemical formula 302a of (C2H6OSi)8H1O1 and a second candidate chemical formula 302b of (C2H6OSi)7C2F2H1N2. As discussed above in relation to FIG. 3A, each candidate chemical formula 302 is associated with a respective score 303 and a respective ppM-error 305. Unfortunately, each score 303 and ppM-error 305 is as bad, if not worse, than the candidate chemical formulas presented in relation to FIG. 3A. In this circumstance, the user may revisit the setup data to continue to interact with the program to identify a candidate chemical formula with high likelihood of a match.

Figure 3D:
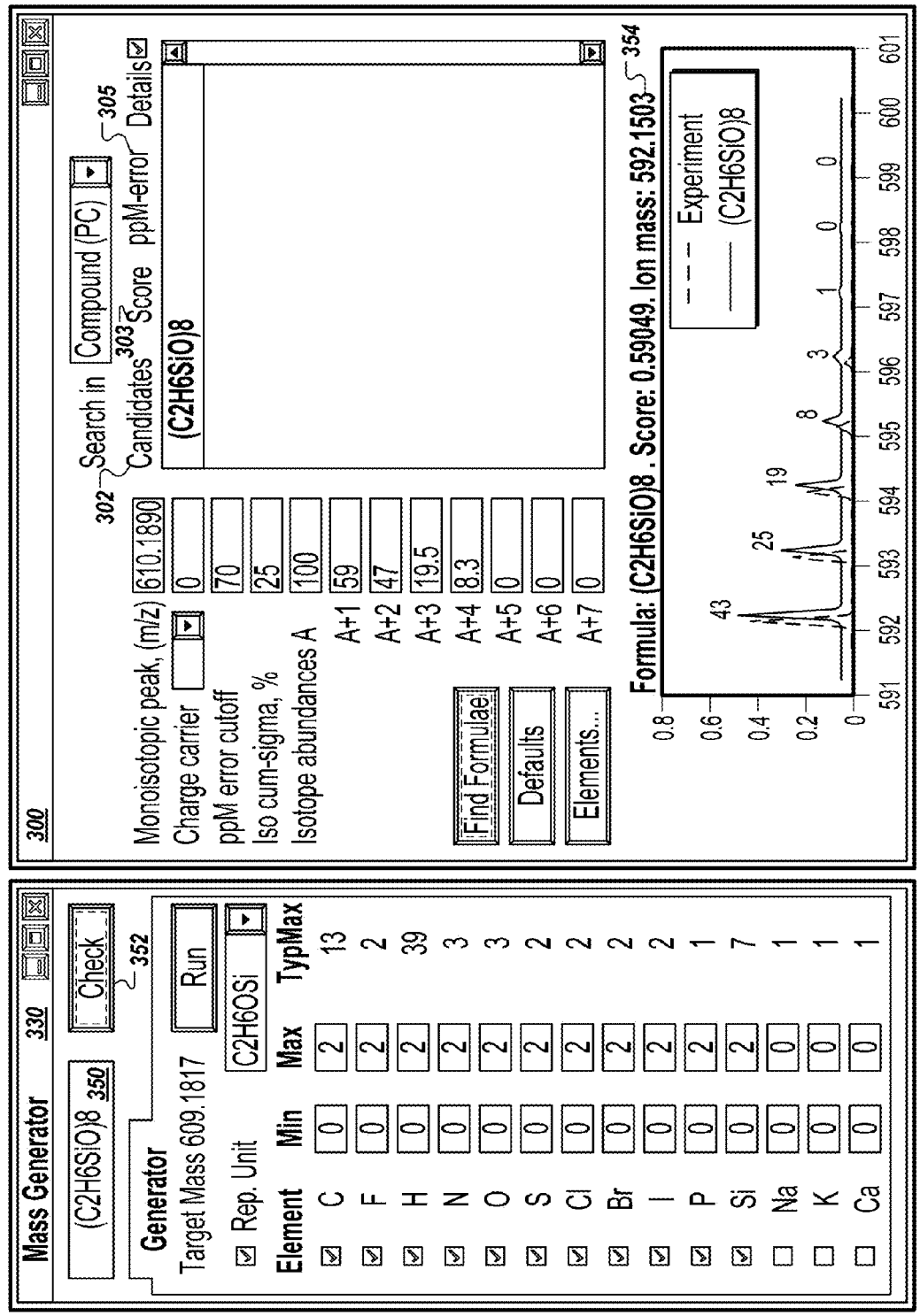

Because the candidate chemical formulas 302 are still not within a range of qualifying as a "match," turning to FIG. 3D, the user may opt to determine statistics regarding the repeating unit alone to better identify a chemical formula of an appropriate end unit. The user may run a comparison of a number of repeating units in relation to the experimental chemical formula. As illustrated in the formula generator window 330, a chemical formula entry field 350 contains a chemical formula of (C2H6SiO)8. In other words, the user is determining whether eight repetitions of the repeating unit comes close to the mass of the experimental chemical formula. The user, for example, may select a "Check" control 352 to obtain results related to the chemical formula of (C2H6SiO)8. As illustrated above the graphical comparison pane 308, responsive to activating the "Check" control 352, a mass 354 of eight repetitions of the repeating unit structure is calculated as 592.1503 Da. Based upon this information, the user may theorize that a charge carrier of ammonium (NH4+) may be more appropriate than the previously attempted charge carrier of a proton (H+). The charge carrier, in typical circumstances, is characteristic of the sample chemistry (e.g. salinity, acidity, etc.), ionization technique type, and mode. When working with known analytes, for example, the charge carrier is immediately revealed. In the particular example illustrated in FIG. 3D, a literature search may have been conducted by the user to identify the possibility of NH4+ as a charge carrier.

Figure 3E:
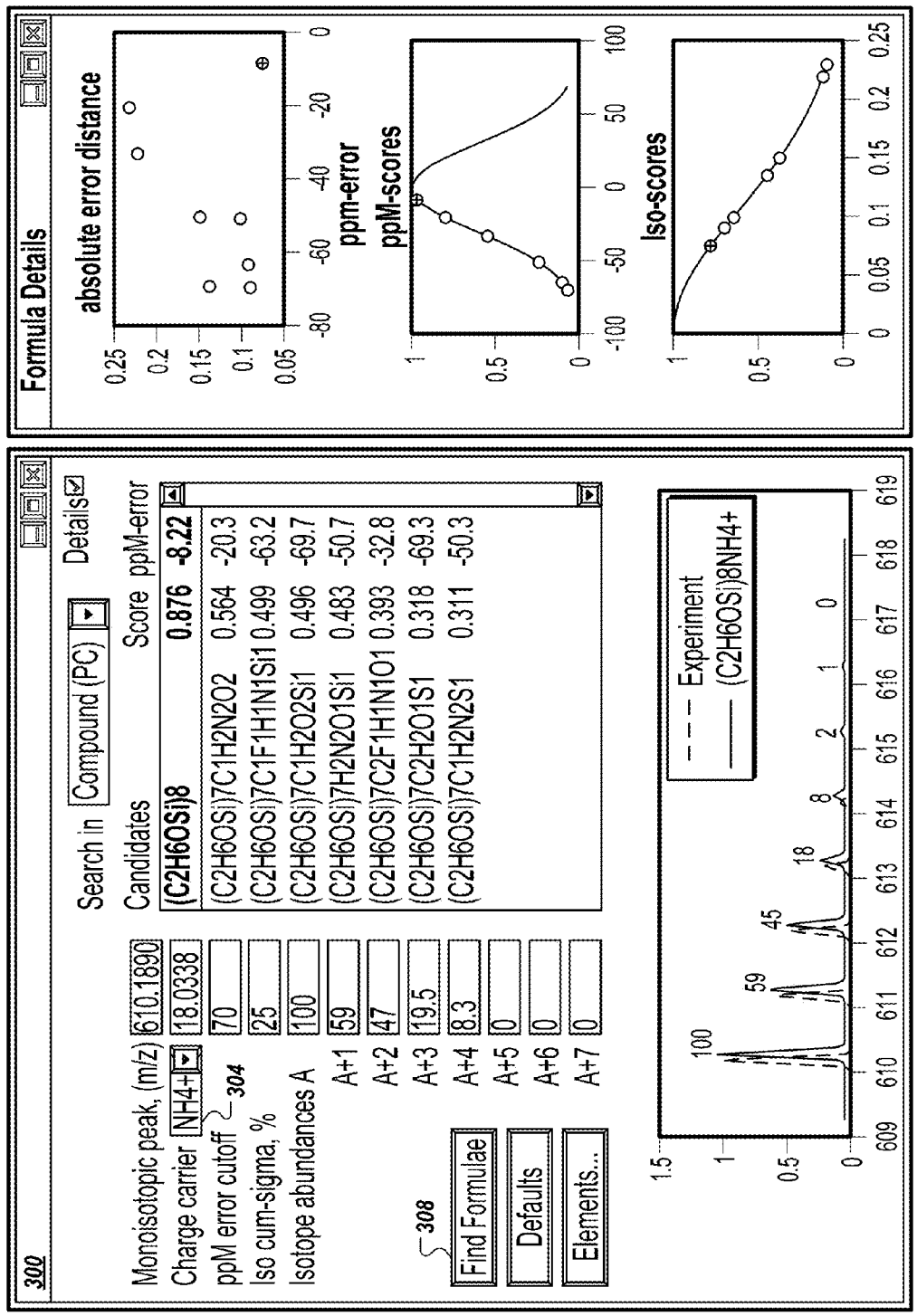

Turning to FIG. 3E, the charge carrier 304 has been changed to ammonium (NH4+). As illustrated within the main window 300, the list of candidate chemical formulas 302 includes a top-ranked candidate chemical formula 302a of an ammonianated octamer, (C2H6OSi)8.

Figure 3F:
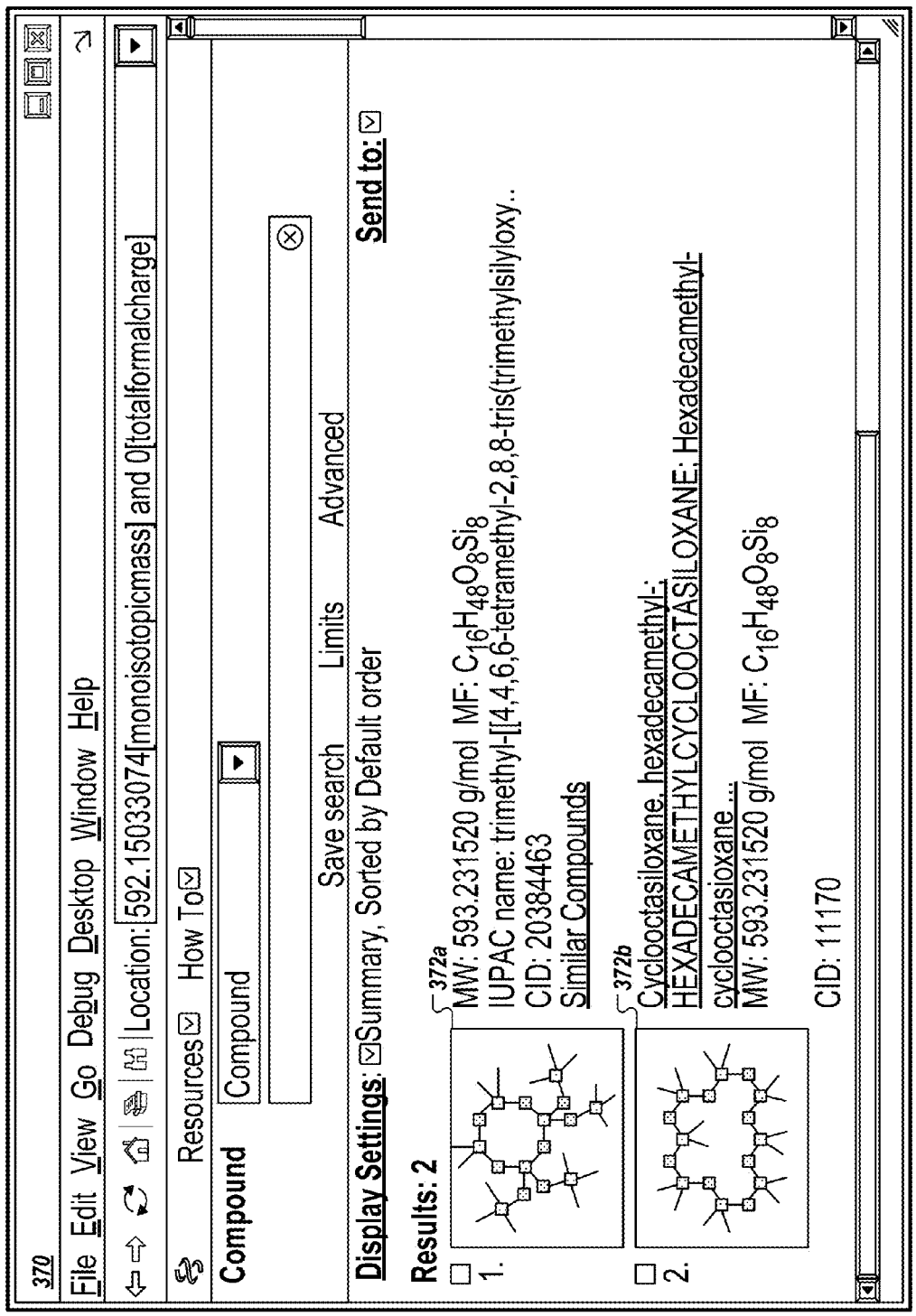

In some implementations, upon selection of one of the candidate chemical formulas 302, a chemical structure selector 370 is displayed, providing one or more candidate chemical structures 372. Turning to FIG. 3F, based upon the candidate chemical formula 302a of an ammonianated octamer, (C2H6OSi)8, two candidate chemical structures 372 are illustrated. In some implementations, the chemical structure selector 370 is presented within a separate browsing unit. For example, while the main window 300, formula statistics window 316, and formula generator window 330 may be presented by the mass spectrometry data analyzer 112, the chemical structure selector 370 may be presented by an engine provided by the chemical structure data store 106, such as a commercial database system, government database system, or standards body database system. The candidate chemical structures 372 are not necessarily ranked in a particular order. For example, unless a distinction between candidate chemical structures 372, such as absence of fragmentation or retention time, may be used to derive a preference between the candidate chemical structures 372, the candidate chemical structures 372 may be considered to each be equally viable. For example, the user may review other types of information regarding the structure of a candidate chemical compound in relation to additional information regarding the experimental compound such as, in some examples, gas-phase chemistry, chromatography, and ion mobility.

In some implementations, candidate chemical structures are based at least in part upon a neutral loss estimate. The neutral loss utility outputs a list of candidates molecular formulas for a parent ion, based on its monoisotopic mass and isotope pattern matched to a database. The user may set a tolerance for the measured mass accuracy as well as confidence in the isotopic ratio measurement. These tolerances enable the user to filter proposed molecular formulas. Upon selection of one of the candidate molecular formulas, the neutral loss utility searches the peak list of the spectrum, calculating mass difference between the theoretical mass of the proposed formulas and the experimental mass of each of a plurality of spectral peaks. For each spectral peak, observed mass difference is compared with masses of molecular compositions in the database. A potential neutral loss match is reported if (i) the difference between the experimental neutral loss and theoretical mass of a molecule is less than the mass measurement accuracy set by the user and (2) stoichiometry of the selected parent ion candidate molecule allows for a proposed neutral loss candidate, i.e., the number of atoms of each type comprising the neutral loss candidate is equal or greater in the current parent ion candidate.

Figure 4A:
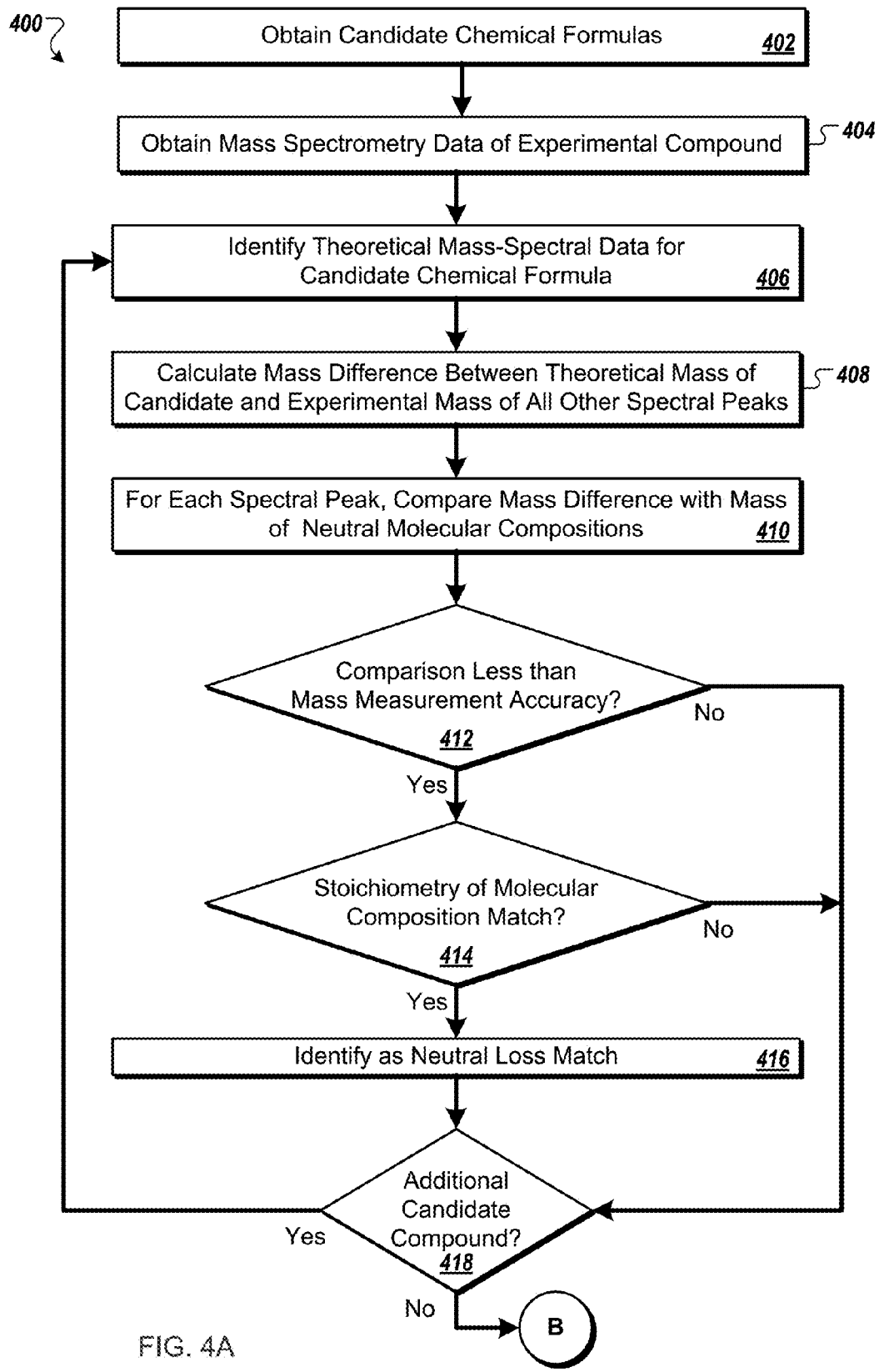
FIGS. 4A and 4B are flow charts of an example method for identification of a chemical formula based at least in part upon neutral loss.
Figure 4B:
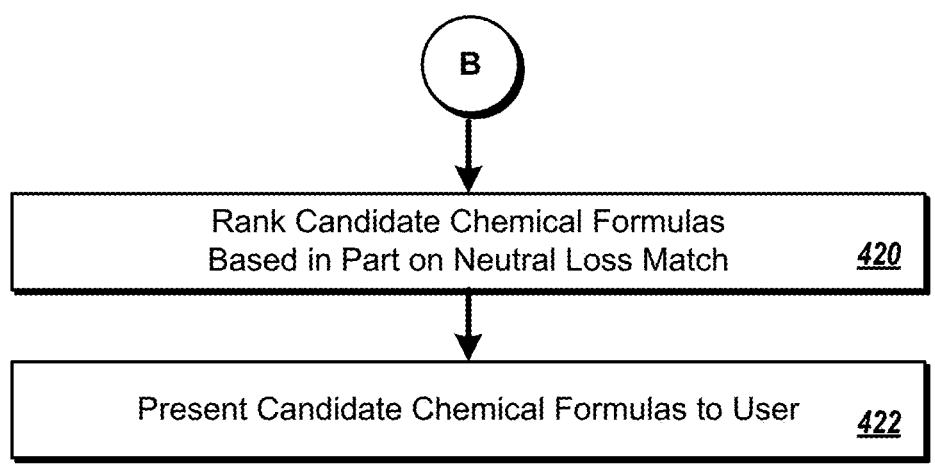

FIGS. 4A and 4B illustrate a flow chart of an example method 400 for identification of a chemical formula based in part upon neutral loss.

In some implementations, the method 400 begins with obtaining candidate chemical formulas (402).

In some implementations, mass spectrometry data of an experimental chemical compound is obtained (402).

In some implementations, theoretical mass-spectral data for a candidate chemical formula is identified (406).

In some implementations, the mass difference between a theoretical mass of the monoisotopic peak of the candidate chemical formula and an experimental mass of all other spectral peaks is calculated (408).

In some implementations, for each spectral peak, the calculated mass difference is compared with a mass of a number of neutral molecular compositions (410).

If, during comparison, it is determined that the mass difference in regards to a particular neutral molecular composition is less than a mass measurement accuracy setting (412), and it is further determined that the stoichiometry of the neutral molecular composition is a match to the candidate chemical formula (414), the particular neutral molecular composition, in some implementations, is identified as a neutral loss match (416). In some implementations, two or more neutral molecular compositions can be identified as neutral loss matches to a particular candidate chemical formula.

In some implementations, if the method 400 is performed in relation to two or more candidate chemical formulas (418), for each candidate chemical formula, the steps 406 through 416 may be repeated.

Turning to FIG. 4B, upon conclusion of identifying the one or more neutral loss matches, in some implementations, the candidate chemical formulas may be ranked in part based upon the results of the neutral loss matching (420). Rather than or in addition to ranking based in part upon the neutral match results, in some implementations, one or more candidate chemical formulas may be discarded from the candidate chemical formulas based upon no neutral loss match being identified.

In some implementations, the candidate chemical formula (s) may be presented to the user (422). The neutral loss match information, in some implementation, may be included within the presentation.

Although the method 400 is illustrated as a particular series of steps, in some implementations, more or fewer steps may be included. Furthermore, in some implementations, one or more of the steps may be executed in a different order than described above. Other modifications are possible without diverging from the spirit and scope of the method 400.

Figure 5A:
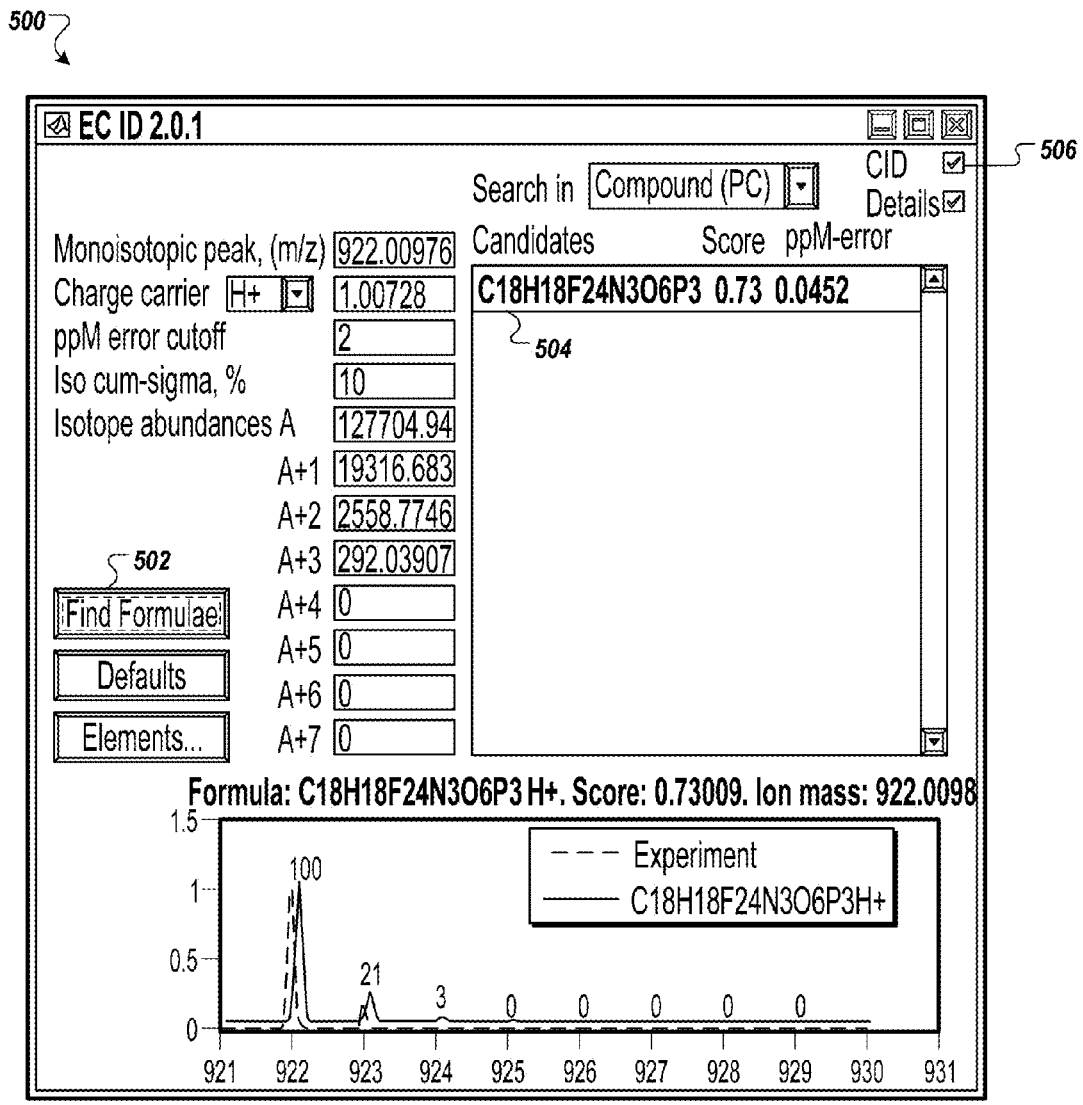
FIGS. 5A and 5B are screen shots of example user interfaces to a system for identification of a chemical compound using a neutral loss method.
Figure 5B:
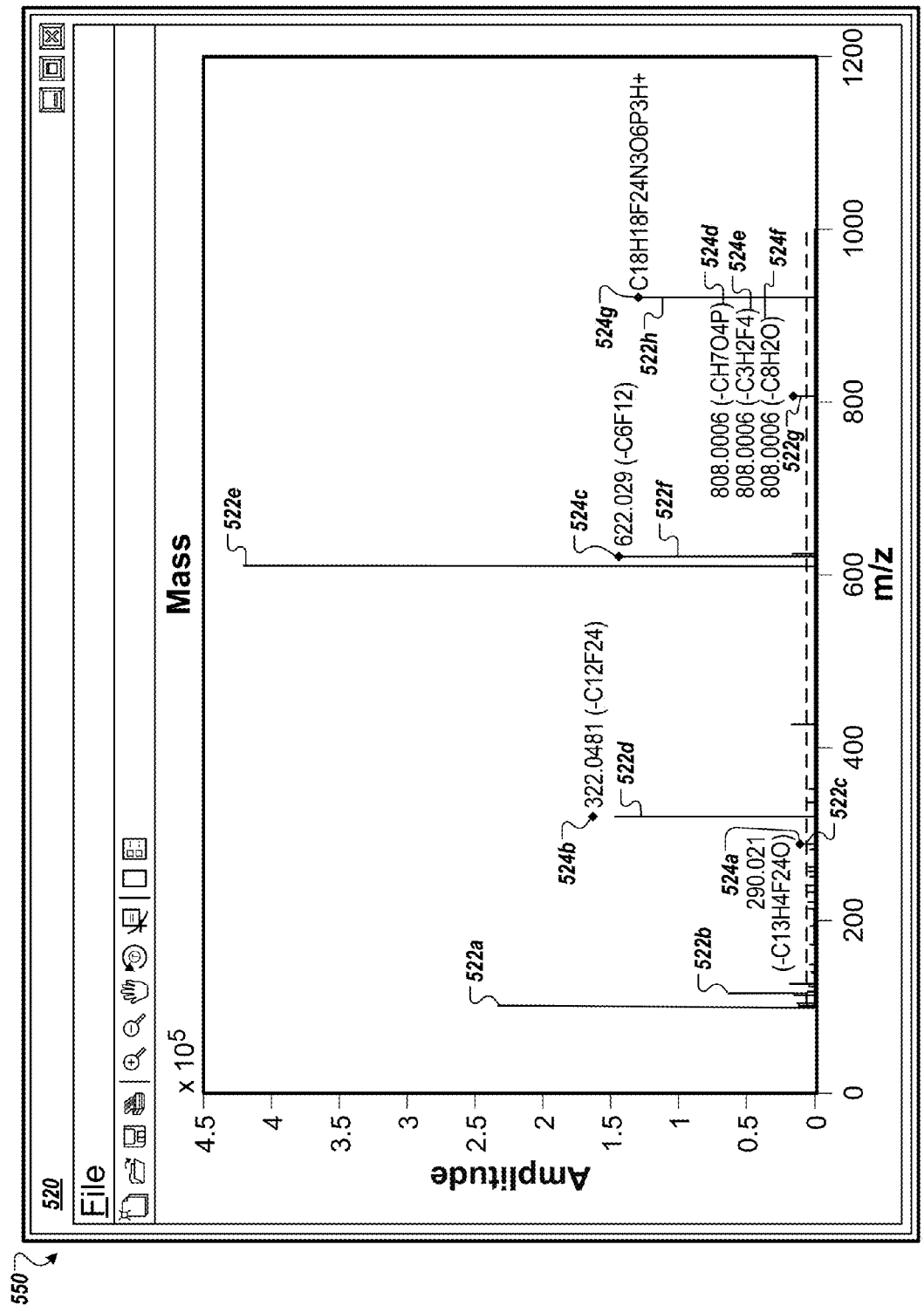

FIGS. 5A and 5B are screen shots of example user interfaces to a system for identification of a chemical compound using a neutral loss method. In some implementations, the screen shots may be generated by the mass spectrometry data analyzer 112, described in relation to FIG. 1. A portion of the information presented in the screen shots, for example, may be produced by the neutral loss calculator 112c, described in relation to FIG. 1.

Turning to FIG. 5A, a main window 500 illustrates an example user interface for identifying one or more candidate chemical formulas based upon analysis of mass spectrometry data. The identification of the candidate chemical formulas, in some implementations, includes a straight iterative analysis, for example as described in relation to the chemical formula identifier 112a of FIG. 1. In some implementations, the identification of the candidate chemical formulas includes an analysis based upon a mass of a repeating unit portion and the identification of potential end unit compositions, for example as described in relation to the formula generator 112b described in relation to FIG. 1. Upon selecting a "find formulae" control 502 within the main window 500, for example, one or more candidate chemical formulas may be identified. As illustrated, one candidate formula 504 was identified.

In the upper right hand corner, a CID (Collision-Induced Dissociation) checkbox 506 has been activated. Due to activation of the CID checkbox 506, in some implementations, a neutral loss matching process may analyze the candidate chemical formula 504 in relation to the mass spectrometry data. The analysis, for example, may include a process similar to a portion of the method 400 described in relation to FIG. 4A.

Based upon identification of a potential neutral loss match, in some implementations, a spectrum interface is presented to the user. Turning to FIG. 5B, a neutral loss spectral analysis screen 520 includes a series of peaks 522. In relation to the peaks 522, any identified fragments matching a neutral molecular composition may be identified with a respective neutral loss formula 524. Note that peak 522g is associated with three neutral loss formulas, namely 524d through 524f.

The following example examines collision induced dissociation in the capillary-skimmer region of a TOF (time-of-flight) mass spectrum. A mass spectrum of an unknown compound with CID fragmentation is obtained. Using the facility described above in relation to FIGS. 2A to 2C, candidates for the unknown compound are identified. The collision induced dissociation (CID) mass spectrum (e.g., theoretical mass-spectral data) for a selected candidate is presented. The elemental composition of the neutral loss for each peak in the mass spectrum is predicted by searching a database and is displayed. By subtracting the neutral loss proposed elemental composition from the parent (candidate) elemental composition, an elemental composition of each of the measured mass spectral peaks can be assigned. A check of the mass and stoichiometry can then result in the identification of the candidate as a neutral loss match for the unknown compound.

Figure 8A:
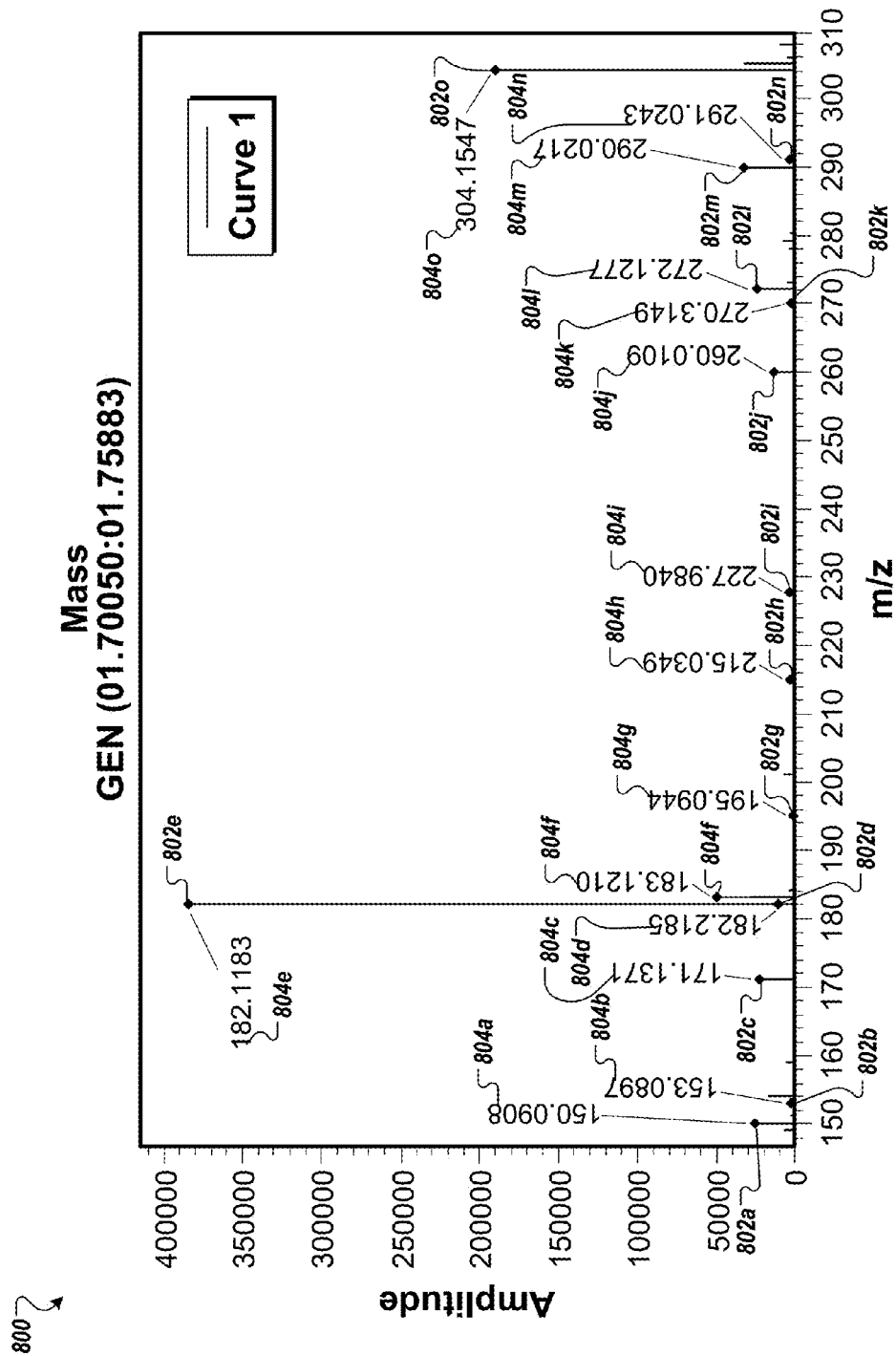
FIGS. 8A through 8D are a series of screen shots demonstrating an example use of a system for identification of a chemical compound using a neutral loss method.

In FIG. 8A, the graph 800 illustrates mass spectrum information for a compound having the chemical formula $C_{17}H_{21}NO_4$ with mass measurement of 304.1547 and collision induced dissociation (CID) fragmentation observed. The graph 800 includes a number of spectral peaks, each spectral peak being associated with a particular amplitude 802 and a particular mass 804. Without knowing the chemical formula for the compound having the mass spectrum information illustrated in the graph 800, using neutral loss analysis, a matching chemical formula candidate may be determined.

Figure 8B:
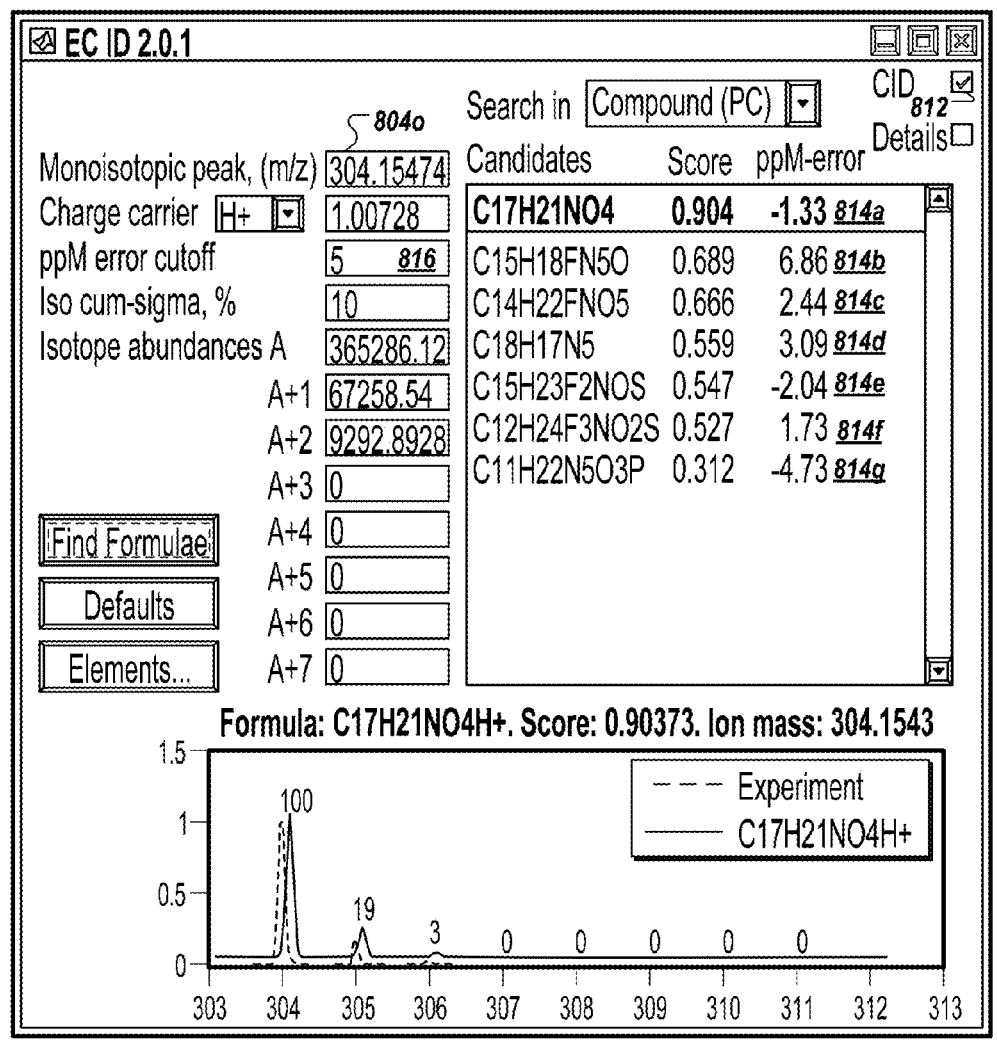

For example, turning to FIG. 8B, a main window 810 illustrates an example user interface for identifying one or more candidate chemical formulas 814 based upon analysis of mass spectrometry data, similar to the main window 500 described in relation to FIG. 5A. In the upper right hand corner, a CID (Collision-Induced Dissociation) checkbox 812 has been activated. Due to activation of the CID checkbox 812, in some implementations, a neutral loss matching process may analyze the candidate chemical formulas 814 in relation to the mass spectrometry data illustrated in graph 800 of FIG. 8A. The analysis, for example, may include a process similar to a portion of the method 400 described in relation to FIG. 4A.

Figure 8C:
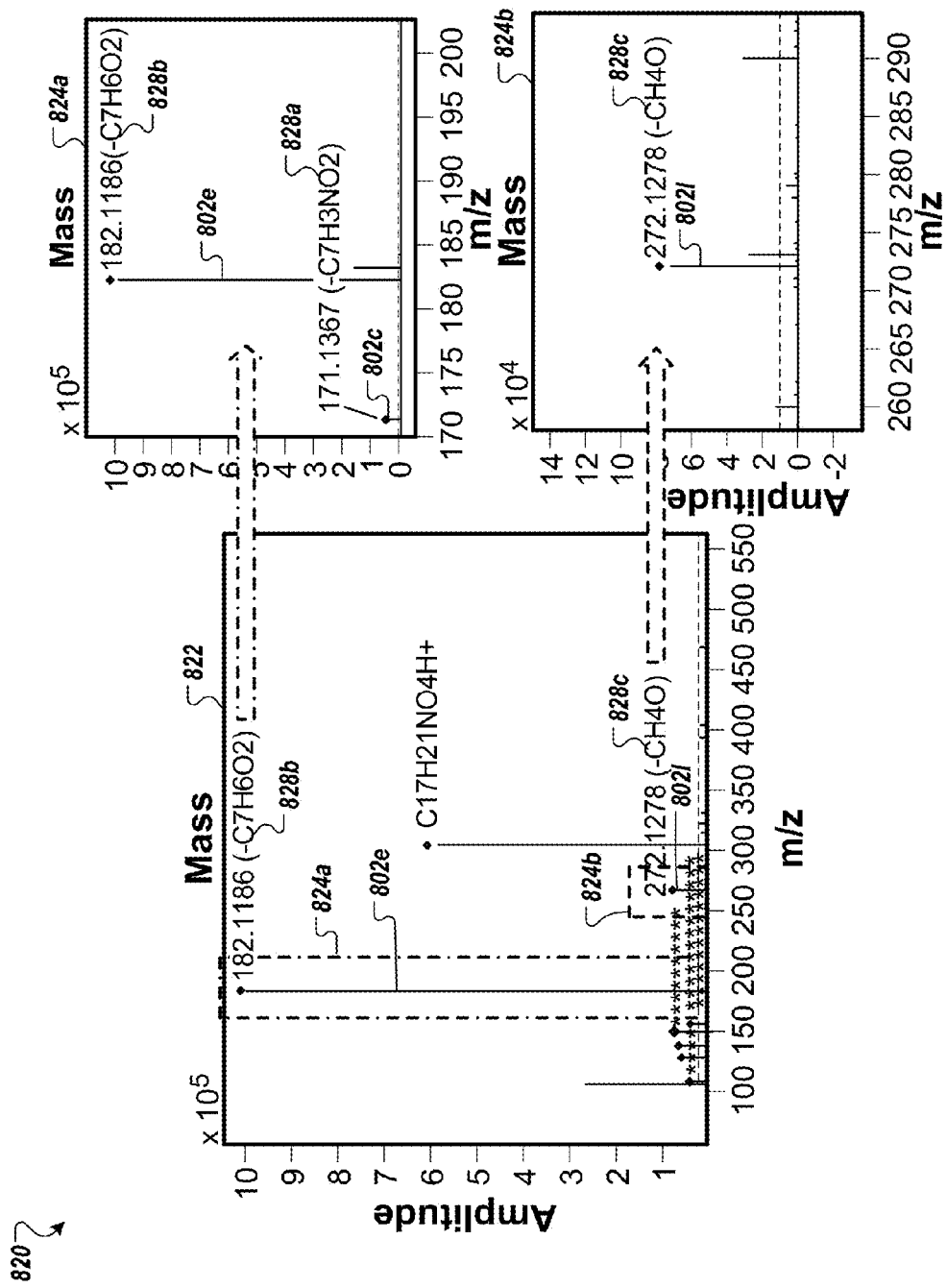

Through the neutral loss analysis, turning to FIG. 8C, an example block diagram 820 illustrates that the elemental composition of the neutral loss for each peak of the graph 800 may be predicted by searching a database for a loss of molecular formula resulting in a neutral, stable molecule having a chemical composition including a portion of the atoms of a candidate chemical formula 814a. Example neutral molecular matches for the peaks of the graph 800 are illustrated in a first neutral loss matching graph 822. Selected from the neutral loss matching graph 822, a first example segment 824a includes the peak 802e having a neutral loss molecular match representing a loss of $C_7H_6O_2$ 828b. The first example segment 824a additionally includes the peak 802c having a neutral loss molecular match representing a loss of $C_7H_3NO_2$ 828a. Turning to a second example segment 824b, the peak 802l has a neutral loss molecular match representing a loss of $CH_4O$ 828c.

Figure 8D:
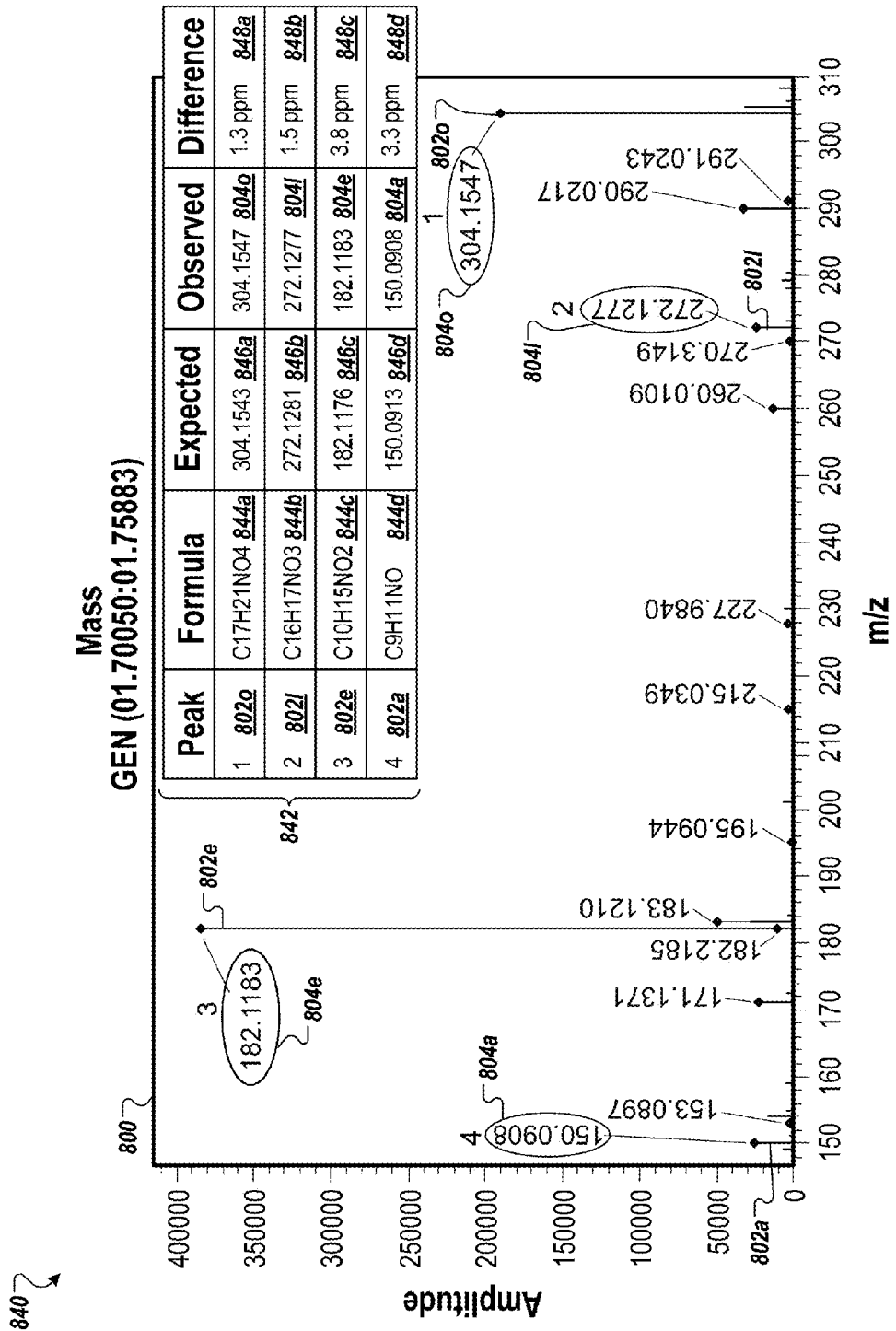

By subtracting the neutral loss proposed elemental composition (e.g., 828a, 828b, 828c) from the parent elemental composition (e.g., $C_{17}H_{21}NO_4$ 814a), an elemental composition corresponding to the measured mass spectral peak can be assigned. Turning to FIG. 8D, a results diagram 840 includes the graph 800 overlaid with a comparison table 842. For each of four example peaks 802a, 802e, 802l, and 802o, a proposed formula 844 has been matched to the observed mass 804. In the example of peak 802l, in subtracting $CH_4O$ 828c (as identified at peak 802e of FIG. 8C) from the parental composition $C_{17}H_{21}NO_4$ 814a, a formula $C_{16}H_{17}NO_3$ 844b is determined. Similarly, for peak 802e, a formula $C_{10}H_{15}NO_2$ 844c is determined by subtracting the chemical compound $C_7H_6O_2$ 828b (of FIG. 8C) from the parental composition $C_{17}H_{21}NO_4$ 814a, and a formula $C_9H_{11}NO$ 844d is determined by subtracting $C_8H_{10}NO_3$ (not illustrated) from the parental composition $C_{17}H_{21}NO_4$ 814a.

In calculating a molecular weight of the proposed formulas 844, a respective expected mass 846 is calculated. In comparing the expected mass 846 to the observed mass 804, a parts-per-million difference 848 is calculated. Turning to FIG. 8B, it may be noted that the ppM difference 848 in each case is within a specified ppM error range 816.

In certain embodiments, methods described herein use data produced by mass spectrometers with any one or more of a variety of mass analyzers, for example, a time-of-flight analyzer, a sector field mass analyzer, a quadrupole mass analyzer, and/or an ion trap. In certain embodiments, methods employ tandem mass spectrometry, and molecule fragmentation is performed using, for example, collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (ED) and/or surface-induced dissociation (SID). In certain embodiments, methods described herein are used in combination with chromatography methods, e.g., GC-MS, LC-MS, and/or IMMS.

As shown in FIG. 6, an implementation of an exemplary cloud computing environment 600 for identification of polymer species from mass spectrometry output is shown and described. The cloud computing environment 600 may include one or more resource providers 602a, 602b, 602c (collectively, 602). Each resource provider 602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 602 may be connected to any other resource provider 602 in the cloud computing environment 600. In some implementations, the resource providers 602 may be connected over a computer network 608. Each resource provider 602 may be connected to one or more computing device 604a, 604b, 604c (collectively, 604), over the computer network 608.

The cloud computing environment 600 may include a resource manager 606. The resource manager 606 may be connected to the resource providers 602 and the computing devices 604 over the computer network 608. In some implementations, the resource manager 606 may facilitate the provision of computing resources by one or more resource providers 602 to one or more computing devices 604. The resource manager 606 may receive a request for a computing resource from a particular computing device 604. The resource manager 606 may identify one or more resource providers 602 capable of providing the computing resource requested by the computing device 604. The resource manager 606 may select a resource provider 602 to provide the computing resource. The resource manager 606 may facilitate a connection between the resource provider 602 and a particular computing device 604. In some implementations, the resource manager 606 may establish a connection between a particular resource provider 602 and a particular computing device 604. In some implementations, the resource manager 606 may redirect a particular computing device 604 to a particular resource provider 602 with the requested computing resource.

Figure 7:
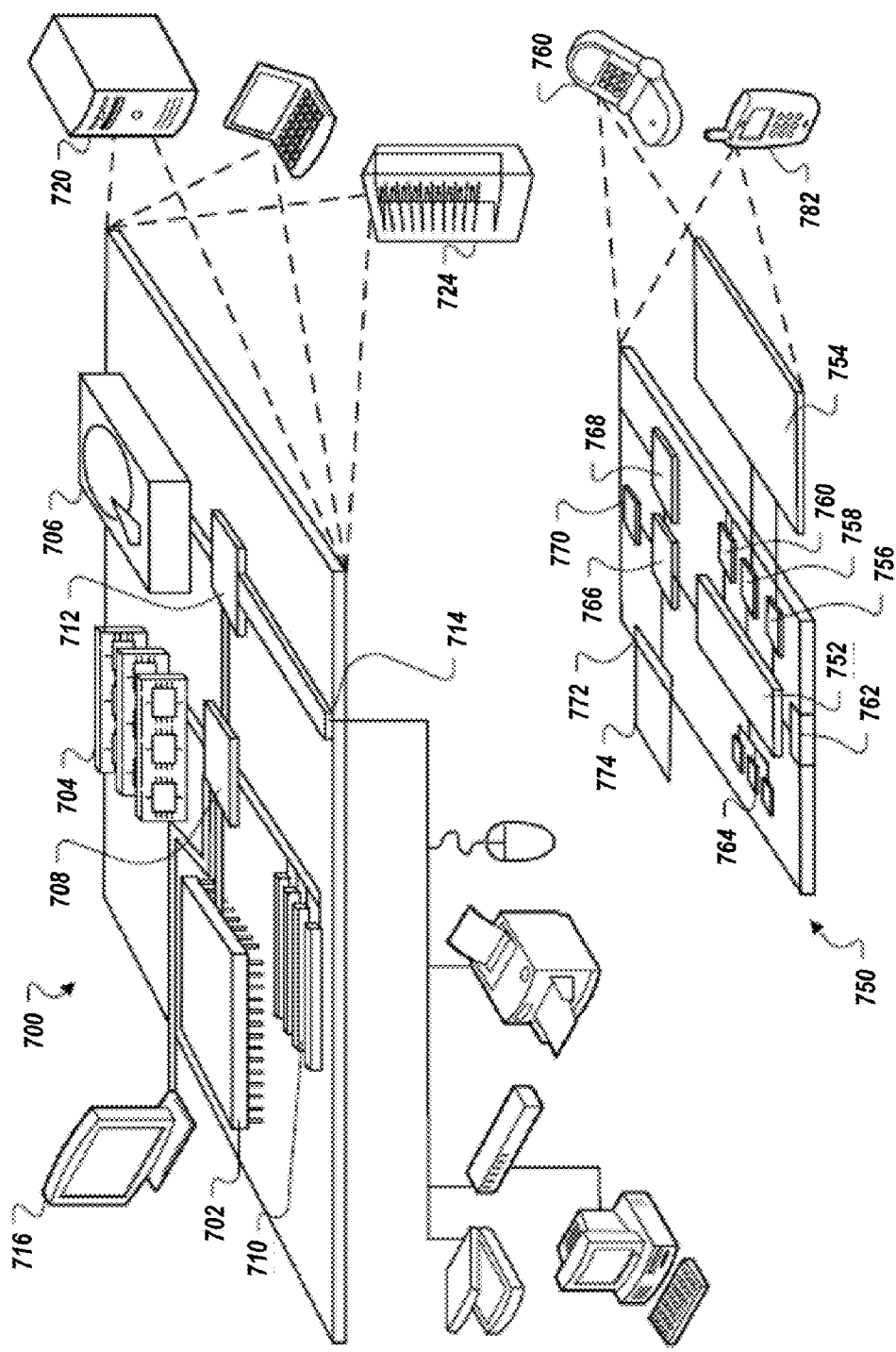
FIG. 7 is a block diagram of an example computing device and an example mobile computing device.

FIG. 7 shows an example of a computing device 700 and a mobile computing device 750 that can be used to implement the techniques described in this disclosure. The computing device 700 is intended to represent various forms of digital computers, such as laptops, desktops, workstations, personal digital assistants, servers, blade servers, mainframes, and other appropriate computers. The mobile computing device 750 is intended to represent various forms of mobile devices, such as personal digital assistants, cellular telephones, smartphones, and other similar computing devices. The components shown here, their connections and relationships, and their functions, are meant to be examples only, and are not meant to be limiting.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 may also be another form of computer-readable medium, such as a magnetic or optical disk.

The storage device 706 is capable of providing mass storage for the computing device 700. In some implementations, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 702), perform one or more methods, such as those described above. The instructions can also be stored by one or more storage devices such as computer- or machine-readable mediums (for example, the memory 704, the storage device 706, or memory on the processor 702).

The high-speed interface 708 manages bandwidth-intensive operations for the computing device 700, while the low-speed interface 712 manages lower bandwidth-intensive operations. Such allocation of functions is an example only. In some implementations, the high-speed interface 708 is coupled to the memory 704, the display 716 (e.g., through a graphics processor or accelerator), and to the high-speed expansion ports 710, which may accept various expansion cards (not shown). In the implementation, the low-speed interface 712 is coupled to the storage device 706 and the low-speed expansion port 714. The low-speed expansion port 714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. In addition, it may be implemented in a personal computer such as a laptop computer 722. It may also be implemented as part of a rack server system 724. Alternatively, components from the computing device 700 may be combined with other components in a mobile device (not shown), such as a mobile computing device 750. Each of such devices may contain one or more of the computing device 700 and the mobile computing device 750, and an entire system may be made up of multiple computing devices communicating with each other.

The mobile computing device 750 includes a processor 752, a memory 764, an input/output device such as a display 754, a communication interface 766, and a transceiver 768, among other components. The mobile computing device 750 may also be provided with a storage device, such as a micro-drive or other device, to provide additional storage. Each of the processor 752, the memory 764, the display 754, the communication interface 766, and the transceiver 768, are interconnected using various buses, and several of the components may be mounted on a common motherboard or in other manners as appropriate.

The processor 752 can execute instructions within the mobile computing device 750, including instructions stored in the memory 764. The processor 752 may be implemented as a chipset of chips that include separate and multiple analog and digital processors. The processor 752 may provide, for example, for coordination of the other components of the mobile computing device 750, such as control of user interfaces, applications run by the mobile computing device 750, and wireless communication by the mobile computing device 750.

The processor 752 may communicate with a user through a control interface 758 and a display interface 756 coupled to the display 754. The display 754 may be, for example, a TFT (Thin-Film-Transistor Liquid Crystal Display) display or an OLED (Organic Light Emitting Diode) display, or other appropriate display technology. The display interface 756 may include appropriate circuitry for driving the display 754 to present graphical and other information to a user. The control interface 758 may receive commands from a user and convert them for submission to the processor 752. In addition, an external interface 762 may provide communication with the processor 752, so as to enable near area communication of the mobile computing device 750 with other devices. The external interface 762 may provide, for example, for wired communication in some implementations, or for wireless communication in other implementations, and multiple interfaces may also be used.

The memory 764 stores information within the mobile computing device 750. The memory 764 can be implemented as one or more of a computer-readable medium or media, a volatile memory unit or units, or a non-volatile memory unit or units. An expansion memory 774 may also be provided and connected to the mobile computing device 750 through an expansion interface 772, which may include, for example, a SIMM (Single In Line Memory Module) card interface. The expansion memory 774 may provide extra storage space for the mobile computing device 750, or may also store applications or other information for the mobile computing device 750. Specifically, the expansion memory 774 may include instructions to carry out or supplement the processes described above, and may also include secure information also. Thus, for example, the expansion memory 774 may be provide as a security module for the mobile computing device 750, and may be programmed with instructions that permit secure use of the mobile computing device 750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 752), perform one or more methods, such as those described above. The instructions can also be stored by one or more storage devices, such as one or more computer- or machine-readable mediums (for example, the memory 764, the expansion memory 774, or memory on the processor 752). In some implementations, the instructions can be received in a propagated signal, for example, over the transceiver 768 or the external interface 762.

The mobile computing device 750 may communicate wirelessly through the communication interface 766, which may include digital signal processing circuitry where necessary. The communication interface 766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 768 using a radio-frequency. In addition, short-range communication may occur, such as using a Bluetooth®, Wi-Fi™, or other such transceiver (not shown). In addition, a GPS (Global Positioning System) receiver module 770 may provide additional navigation- and location-related wireless data to the mobile computing device 750, which may be used as appropriate by applications running on the mobile computing device 750.

The mobile computing device 750 may also communicate audibly using an audio codec 760, which may receive spoken information from a user and convert it to usable digital information. The audio codec 760 may likewise generate audible sound for a user, such as through a speaker, e.g., in a handset of the mobile computing device 750. Such sound may include sound from voice telephone calls, may include recorded sound (e.g., voice messages, music files, etc.) and may also include sound generated by applications operating on the mobile computing device 750.

The mobile computing device 750 may be implemented in a number of different forms, as shown in the figure. For example, it may be implemented as a cellular telephone 780. It may also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for identification of polymer species from mass spectrometry output are provided. Having described certain implementations of methods and apparatus for supporting identification of polymer species from mass spectrometry output, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A method for identifying a species of an unidentified chemical compound comprising repeating structural units, and one or more end units, the method comprising:
    accessing at least a portion of mass spectrometry data, wherein the portion of mass spectrometry data relates to a sample comprising the unidentified chemical compound;
    identifying an estimated mass of the unidentified chemical compound;
    determining an estimated mass of the portion of the unidentified chemical compound made up of the repeating structural units; and
    identifying, by a processor of a computing device, one or more candidate chemical formulas for the unidentified chemical compound based at least in part on:
        (i) the mass spectrometry data for the unidentified chemical compound;
        (ii) the estimated mass of the unidentified chemical compound; and
        (iii) the estimated mass of the portion of the unidentified chemical compound made up of the repeating structural units.

2. The method of claim 1, wherein
each repeating structural unit has the same chemical formula.

3. The method of claim 1, further comprising determining a set of candidate chemical elements from which the chemical formula(s) of the one or more end units is composed and limited to.

4. The method of claim 3, further comprising determining a maximum number of each chemical element in the set of candidate chemical elements, wherein the chemical formula(s) of the one or more end units, taken together, comprise(s) no more than the maximum number of each chemical element in the set of candidate chemical elements.

5. The method of claim 4, wherein identifying the one or more candidate chemical formulas for the unidentified chemical compound comprises determining the chemical formula(s) of the one or more end units based at least in part on the set of candidate chemical elements and the determined maximum number of each chemical element in the set of candidate elements.

6. The method of claim 1, wherein identifying the one or more candidate chemical formulas for the unidentified chemical compound comprises iteratively assembling combinations of elements to identify a plurality of candidate element combinations for the one or more end units, wherein a calculated mass of each candidate element combination of the plurality of candidate element combinations, when summed with the estimated mass of the portion of the unidentified chemical compound made up of the repeating units, is within a threshold mass of the estimated mass of the unidentified chemical compound.

7. The method of claim 6, comprising calculating the estimated mass of the portion of the unidentified chemical compound made up of the repeating units by:
    calculating a mass of a first candidate chemical formula of the repeating units, and
    multiplying the mass of the first candidate chemical formula by an estimated number of repetitions.

8. The method of claim 1, further comprising, after identifying the one or more candidate chemical formulas for the unidentified chemical compound, for each candidate chemical formula of the one or more candidate chemical formulas:
    calculating theoretical mass spectrometry data for the respective candidate chemical formula;
    comparing the theoretical mass spectrometry data for the respective candidate chemical formula to experimental mass spectrometry data of the portion of mass spectrometry data; and
    either (a) ranking the one or more candidate chemical formulas, or (b) discarding one or more of the one or more candidate chemical formulas based at least in part on the comparison of the theoretical mass spectrometry data of each candidate chemical formula to the experimental mass spectrometry data of the portion of mass spectrometry data.

9. The method of claim 1, further comprising presenting the one or more candidate chemical formulas to a user within a graphical user interface.

10. A system comprising:
    a processor; and
    a memory storing instructions thereon, wherein the instructions when executed cause the processor to:
        access at least a portion of mass spectrometry data, wherein the portion of mass spectrometry data relates to a sample comprising an unidentified chemical compound, wherein the unidentified chemical compound comprises repeating structural units and one or more end units;
        identify an estimated mass of the unidentified chemical compound;
        determine an estimated mass of the portion of the unidentified chemical compound made up of the repeating structural units; and identify one or more candidate chemical formulas for the unidentified chemical compound based at least in part on:
(i) the mass spectrometry data for the unidentified chemical compound;
(ii) the estimated mass of the unidentified chemical compound; and
(iii) the estimated mass of the portion of the unidentified chemical compound made up of the repeating structural units.

11. The system of claim 10, wherein each repeating structural unit has the same chemical formula.

12. The system of claim 10, wherein the instructions further cause the processor to:
determine a first candidate chemical formula of the one or more candidate chemical formulas is a neutral loss match to the unidentified chemical compound, said determining of the neutral loss match comprising:
accessing mass spectrometry data for the first candidate chemical formula, and
for each of a plurality of spectral peaks of the mass spectrometry data for the first candidate chemical formula:
calculating a respective mass difference between a theoretical mass of the first candidate chemical formula and a respective experimental mass corresponding to the spectral peak, and
comparing the respective mass difference with a mass of each of one or more corresponding neutral molecular compositions to identify one or more candidate neutral molecular compositions corresponding to the spectral peak.

13. The system of claim 12, wherein the mass spectrometry data comprises a collision-induced dissociation (CID) mass spectrum.

14. The system of claim 12, the instructions further causing the processor to:
determine a second candidate chemical formula is a neutral loss match to the unidentified chemical compound; and
rank the first candidate chemical formula and the second candidate chemical formula as matches to the unknown chemical compound based in part upon similarity in neutral loss match.

15. The system of claim 12, wherein identifying the one or more candidate neutral molecular compositions comprises identifying that each candidate neutral molecular composition of the one or more candidate neutral molecular compositions comprises a respective mass within range of a mass measurement accuracy of the respective experimental mass of the spectral peak.

16. The system of claim 12, wherein determining that the first candidate chemical formula is a neutral loss match to the unidentified chemical compound comprises identifying that a stoichiometry of the first candidate chemical formula allows for at least a first candidate neutral molecular composition of the one or more candidate neutral molecular compositions.

17. The system of claim 16, wherein identifying that the stoichiometry of the first candidate formula allows for the first candidate neutral molecular composition comprises determining, for the first candidate neutral molecular composition, that a number of atoms of each type in the first candidate chemical formula is greater than a number of atoms of each corresponding type in the candidate neutral loss composition.

18. A non-transitory computer readable medium having instructions stored thereon that, when executed by a processor, cause the processor to:
access at least a portion of mass spectrometry data, wherein the portion of mass spectrometry data relates to a sample comprising an unidentified chemical compound, wherein the unidentified chemical compound comprises repeating structural units, and one or more end units;
identify an estimated mass of the unidentified chemical compound;
determine an estimated mass of the portion of the unidentified chemical compound made up of the repeating structural units; and
identify one or more candidate chemical formulas for the unidentified chemical compound based at least in part on:
(i) the mass spectrometry data for the unidentified chemical compound;
(ii) the estimated mass of the unidentified chemical compound; and
(iii) the estimated mass of the portion of the unidentified chemical compound made up of the repeating structural units.

19. The method of claim 1, wherein each of the one or more end units has a chemical formula different than the chemical formula of the repeating structural units.

20. The method of claim 1, comprising generating the mass spectrometry data for the sample comprising the unidentified chemical compound using a mass spectrometer.

21. The method of claim 1, wherein identifying the estimated mass of the unidentified chemical compound comprises determining an accurate mass from the mass spectrometry data.

22. The method of claim 21, wherein identifying the estimated mass of the unidentified chemical compound comprises determining the accurate mass from a monoisotopic peak corresponding to the unidentified chemical compound.

23. The method of claim 22, wherein identifying the estimated mass of the unidentified chemical compound comprises determining the accurate mass from a monoisotopic peak corresponding to the unidentified chemical compound calculated as a centroid of a profile peak of the mass spectrometry data.

24. The method of claim 8, wherein comparing the theoretical mass spectrometry data of each candidate chemical formula of the one or more candidate chemical formulas to the experimental mass spectrometry data of the portion of mass spectrometry data comprises calculating a difference between the theoretical monoisotopic mass of the candidate chemical formula and the accurate mass of the monoisotopic peak of the unidentified chemical compound.

25. The method of claim 8, wherein comparing the theoretical mass spectrometry data of each candidate chemical formula of the one or more candidate chemical formulas to the experimental mass spectrometry data of the portion of mass spectrometry data comprises calculating a difference between the theoretical relative abundance of isotopes of a candidate molecular formula and the experimental relative abundance of isotopes.

* * * * *